(12) United States Patent
Matsushita

(10) Patent No.: US 9,168,208 B2
(45) Date of Patent: Oct. 27, 2015

(54) ULTRAVIOLET-SHIELDING COMPOSITE PARTICLES, METHOD FOR MANUFACTURING THE SAME, ULTRAVIOLET-SHIELDING COMPOSITE PARTICLE-CONTAINING DISPERSION LIQUID, AQUEOUS DISPERSION ELEMENT, OIL-BASED DISPERSION ELEMENT AND COSMETIC MATERIAL

(75) Inventor: Hirokazu Matsushita, Tokyo (JP)

(73) Assignee: SUMITOMO OSAKA CEMENT CO., LTD. (JP)

( * ) Notice: Subject to any disclaimer, the term of this patent is extended or adjusted under 35 U.S.C. 154(b) by 0 days.

(21) Appl. No.: 13/981,178

(22) PCT Filed: Jan. 25, 2012

(86) PCT No.: PCT/JP2012/051517
§ 371 (c)(1),
(2), (4) Date: Oct. 3, 2013

(87) PCT Pub. No.: WO2012/102296
PCT Pub. Date: Aug. 2, 2012

(65) Prior Publication Data
US 2014/0017288 A1   Jan. 16, 2014

(30) Foreign Application Priority Data
Jan. 25, 2011   (JP) ................................. 2011-012859

(51) Int. Cl.
| | | |
|---|---|---|
| *A61K 9/14* | (2006.01) | |
| *A61K 8/02* | (2006.01) | |
| *A61K 8/27* | (2006.01) | |
| *A61K 8/29* | (2006.01) | |
| *A61Q 17/04* | (2006.01) | |
| *A61K 8/19* | (2006.01) | |
| *A61K 8/35* | (2006.01) | |
| *A61K 8/81* | (2006.01) | |

(52) U.S. Cl.
CPC ............ *A61K 8/0241* (2013.01); *A61K 8/0283* (2013.01); *A61K 8/19* (2013.01); *A61K 8/27* (2013.01); *A61K 8/29* (2013.01); *A61K 8/35* (2013.01); *A61K 8/8152* (2013.01); *A61Q 17/04* (2013.01); *A61K 2800/412* (2013.01)

(58) Field of Classification Search
None
See application file for complete search history.

(56) References Cited

U.S. PATENT DOCUMENTS

| | | | | |
|---|---|---|---|---|
| 6,200,680 | B1 * | 3/2001 | Takeda et al. ................ | 428/402 |
| 8,673,329 | B2 * | 3/2014 | Yamada et al. .............. | 424/401 |
| 8,728,503 | B2 * | 5/2014 | Yamada et al. .............. | 424/401 |
| 2006/0167138 | A1 * | 7/2006 | Ishii et al. .................... | 523/200 |
| 2009/0098206 | A1 * | 4/2009 | Kessell et al. ................ | 424/489 |
| 2012/0177707 | A1 * | 7/2012 | Matsushita et al. .......... | 424/401 |

FOREIGN PATENT DOCUMENTS

| | | | |
|---|---|---|---|
| JP | A-09-208437 | 8/1997 | |
| JP | A-09-208864 | 8/1997 | |
| JP | A-09-208927 | 8/1997 | |
| JP | A-11-189520 | 7/1999 | |
| JP | B-3205249 | 9/2001 | |
| JP | A-2002-256008 | 9/2002 | |
| JP | A-2003-238606 | 8/2003 | |
| JP | B-3469641 | 11/2003 | |
| JP | 2004182984 A | * | 7/2004 |
| JP | A-2004-182984 | 7/2004 | |
| WO | WO 2010/098249 A1 | 9/2010 | |
| WO | WO 2011/034032 A1 | 3/2011 | |

OTHER PUBLICATIONS

International Search Report for corresponding International Patent Application No. PCT/JP2012/051517 (mailed Apr. 24, 2012).

* cited by examiner

*Primary Examiner* — Robert A Wax
*Assistant Examiner* — Olga V Tchderkasskaya
(74) *Attorney, Agent, or Firm* — Merchant & Gould P.C.

(57) ABSTRACT

Ultraviolet-shielding composite particles of the invention are ultraviolet-shielding composite particles which include a resin containing an organic ultraviolet absorbent and metal oxide particles having an ultraviolet-shielding function, and have an average particle diameter of 0.05 μm or more and 5 μm or less, in which the metal oxide particles are particles which include one or two or more selected from the group consisting of zinc oxide, titanium oxide, cerium oxide and iron oxide and have an average particle diameter of 0.003 μm or more and 0.1 μm or less, a content of the organic ultraviolet absorbent in the ultraviolet-shielding composite particles is 0.1% by mass or more 80% by mass or less, a content of the metal oxide particles is 1% by mass or more 80% by mass or less, and the metal oxide particles are dispersed in the ultraviolet-shielding composite particles.

14 Claims, 12 Drawing Sheets

ULTRAVIOLET-SHIELDING COMPOSITE PARTICLES, METHOD FOR MANUFACTURING THE SAME, ULTRAVIOLET-SHIELDING COMPOSITE PARTICLE-CONTAINING DISPERSION LIQUID, AQUEOUS DISPERSION ELEMENT, OIL-BASED DISPERSION ELEMENT AND COSMETIC MATERIAL

This application is a U.S. National Stage Application under 35 U.S.C. §371 of International Patent Application No. PCT/JP2012/051517 filed 25 Jan. 2012, which claims the benefit of priority to Japanese Patent Application No. 2011/012859 filed 25 Jan. 2011, the disclosures of all of which are hereby incorporated by reference in their entireties. The International Application was published in Japanese on 2 Aug. 2012 as WO 2012/102296.

TECHNICAL FIELD

The present invention relates to ultraviolet-shielding composite particles, a method for manufacturing the same, an ultraviolet-shielding composite particle-containing dispersion liquid, an aqueous dispersion element, an oil-based dispersion element and a cosmetic material, and, more specifically, to ultraviolet-shielding composite particles preferable for a variety of cosmetic products, such as skin care cosmetic products, makeup cosmetic products and body care cosmetic products, particularly for whitening by skin care cosmetic products, base-making by makeup cosmetic products and sun-screening by body care cosmetic products, for which an ultraviolet-shielding function is required, a method for manufacturing the same, an ultraviolet-shielding composite particle-containing dispersion liquid, an aqueous dispersion element, an oil-based dispersion element and a cosmetic material, all of which include the ultraviolet-shielding composite particles.

BACKGROUND

In the past, as an ultraviolet-shielding material used in cosmetic products, there were inorganic ultraviolet-shielding agents and organic ultraviolet absorbents, and a suitable ultraviolet-shielding agent has been selectively used depending on use.

Since the wavelengths of ultraviolet rays, which can be shielded by inorganic ultraviolet-shielding agents and organic ultraviolet absorbents, differ depending on the kinds thereof, a cosmetic material is preferably formulated by appropriately combining both kinds of agents.

However, when inorganic ultraviolet-shielding agents and organic ultraviolet absorbents were jointly used, since the organic ultraviolet absorbents were recrystallized due to the influence of metal ions, and thus the alteration and discoloration of the cosmetic material and the impairment in a feeling of using the product occurred, there was a problem in that a cosmetic material could not be formulated by freely mixing inorganic ultraviolet-shielding agents and organic ultraviolet absorbents.

In order to solve the above problem, spherical resin powder which includes an inorganic ultraviolet-shielding agent at 1% by mass to 80% by mass of the total mass, has a particle diameter of 30 µm or less, and has an ultraviolet-shielding function (Patent Citation 1), resin powder obtained by dispersing a metal oxide having an ultraviolet-shielding function in resin monomers and performing suspension polymerization or emulsion polymerization (Patent Citation 2) and the like have been proposed, and a cosmetic material was formulated while avoiding the direct contact between inorganic ultraviolet-shielding agents and organic ultraviolet absorbents.

CITATION LIST

Patent Literature

[Patent Citation 1] Japanese Patent No. 3469641
[Patent Citation 2] Japanese Patent No. 3205249

SUMMARY OF INVENTION

Problem to be Solved by the Invention

However, with an organic ultraviolet absorbent of the related art, there was a problem in that, when a person with sensitive skin repetitively used the absorbent, there was a concern of influences on skin, such as the occurrence of allergic symptoms.

In addition, since the organic ultraviolet absorbent is insoluble in water, in order for the absorbent to exhibit the ultraviolet-shielding function, it is necessary to dissolve the agent in a specific solvent, and thus, in a case where a cosmetic material was formulated by mixing inorganic ultraviolet-shielding agents and organic ultraviolet absorbents, there were problems in that it was difficult to formulate a cosmetic material by mixing agents, it was difficult to formulate particularly an aqueous cosmetic material by mixing agents, and the degree of freedom for the formulation of a cosmetic material decreased.

The invention has been made in consideration of the above circumstances, and an object of the invention is to provide ultraviolet-shielding composite particles which enable the formulation of a cosmetic material by mixing inorganic ultraviolet-shielding agents and organic ultraviolet absorbents, reduces the contact of an organic ultraviolet absorbent with skin, and can be blended not only into a water-in-oil (W/O) cosmetic material but also into an oil-in-water (O/W) cosmetic material, a method for manufacturing the same, an ultraviolet-shielding composite particle-containing dispersion liquid, an aqueous dispersion element, an oil-based dispersion element, and a cosmetic material.

Means for Solving the Problem

As a result of repeating thorough studies in order to solve the above problems, the present inventors and the like found that, when metal oxide particles, which are an inorganic ultraviolet-shielding agent, are mixed with an organic ultraviolet absorbent in resin monomers, and the resin monomers are polymerized through suspension polymerization or emulsion polymerization, thereby producing fine composite particles, the organic ultraviolet absorbent does not need to be dissolved in a specific solvent, and, furthermore, the fine composite particles can also be applied to the formulation of an aqueous cosmetic product, and completed the invention.

That is, ultraviolet-shielding composite particles of the invention are ultraviolet-shielding composite particles which include a resin containing an organic ultraviolet absorbent and metal oxide particles having an ultraviolet-shielding function, and have an average particle diameter of 0.05 µm or more and 5 µm or less, in which the metal oxide particles are particles which include one or two or more selected from the group consisting of zinc oxide, titanium oxide, cerium oxide and iron oxide and have an average particle diameter of 0.003

µm or more and 0.1 µm or less, a content of the organic ultraviolet absorbent in the ultraviolet-shielding composite particles is 0.1% by mass or more and 80% by mass or less, a content of the metal oxide particles is 1% by mass or more and 80% by mass or less, and the metal oxide particles are dispersed in the ultraviolet-shielding composite particles.

The resin is preferably a (meth)acrylic resin.

The organic ultraviolet absorbent is preferably one or two or more selected from the group consisting of dibenzoyl methane-based compounds, benzophenone derivatives, para-aminobenzoic acid derivatives, methoxycinnamic acid derivatives and salicylic acid derivatives.

In one method of methods for manufacturing ultraviolet-shielding composite particles of the invention, metal oxide particles having an average particle diameter of 0.003 µm or more and 0.1 µm or less and an ultraviolet-shielding function are dispersed in 1% by mass or more and 50% by mass or less of dispersant-containing resin monomers with respect to the metal oxide particles to produce a resin monomer dispersion liquid containing the metal oxide particles, then, 0.1% by mass or more and 80% by mass or less of an organic ultraviolet absorbent is dissolved in the resin monomer dispersion liquid to produce a resin monomer-dissolved liquid containing the metal oxide particles and the organic ultraviolet-shielding absorbent, then, the resin monomer-dissolved liquid is suspended or emulsified in pure water including a suspension protectant, a silicone-based defoamer and a crosslinking agent to produce a suspended liquid or an emulsified liquid, and then a polymerization initiator is added to the suspended liquid or the emulsified liquid to perform suspension polymerization or emulsion polymerization, thereby generating ultraviolet-shielding composite particles.

In another method for manufacturing ultraviolet-shielding composite particles of the invention, 0.1% by mass or more and 80% by mass or less of an organic ultraviolet absorbent is dissolved to produce a resin monomer-dissolved liquid containing the organic ultraviolet absorbent, then, 1% by mass or more and 80% by mass or less of metal oxide particles having an average particle diameter of 0.003 µm or more and 0.1 µm or less and an ultraviolet-shielding function are dispersed in the resin monomer-dissolved liquid to produce a resin monomer dispersion liquid containing the metal oxide particles and the organic ultraviolet absorbent, then, the resin monomer dispersion liquid is suspended or emulsified in pure water including a suspension protectant, a silicone-based defoamer and a crosslinking agent to produce a suspended liquid or an emulsified liquid, and then a polymerization initiator is added to the suspended liquid or the emulsified liquid to perform suspension polymerization or emulsion polymerization, thereby generating ultraviolet-shielding composite particles.

An ultraviolet-shielding composite particle-containing dispersion liquid of the invention is an ultraviolet-shielding composite particle-containing dispersion liquid with the ultraviolet-shielding composite particles of the invention being dispersed in a dispersion medium, in which a content of the ultraviolet-shielding composite particles is 1% by mass or more and 80% by mass or less.

An ultraviolet-shielding composite particle-containing aqueous dispersion element of the invention is an ultraviolet-shielding composite particle-containing aqueous dispersion element with the ultraviolet-shielding composite particles of the invention being dispersed in a dispersion medium including alcohols, in which a content of the ultraviolet-shielding composite particles is 1% by mass or more and 80% by mass or less, and a content of the alcohols is 5% by mass or more and 20% by mass or less.

An ultraviolet-shielding composite particle-containing oil-based dispersion element of the invention is an ultraviolet-shielding composite particle-containing oil-based dispersion element with the ultraviolet-shielding composite particles of the invention being dispersed in an oily component including a surfactant, in which a content of the ultraviolet-shielding composite particles is 1% by mass or more and 80% by mass or less, a content of the oily component is 10% by mass or more and 90% by mass or less, and a content of the surfactant is 1% by mass or more and 40% by mass or less.

A cosmetic material of the invention contains 1% by mass or more and 60% by mass or less of one or two or more selected from the group consisting of the ultraviolet-shielding composite particles of the invention, the ultraviolet-shielding composite particle-containing dispersion liquid of the invention, the ultraviolet-shielding composite particle-containing aqueous dispersion element of the invention and the ultraviolet-shielding composite particle-containing oil-based dispersion element of the invention in terms of the ultraviolet-shielding composite particles.

Effects of the Invention

According to the ultraviolet-shielding composite particles of the invention, since the organic ultraviolet absorbent and the metal oxide particles having an ultraviolet-shielding function are fixed in the resin, it is possible to prevent the alteration and discoloration of the cosmetic material and the impairment in a feeling of using the product, which are caused by the recrystallization of the organic ultraviolet absorbent due to the influence of metal ions. Furthermore, since the burden for skin contacted with the organic ultraviolet absorbent is reduced, the particles are highly safe with respect to the human body, and thus it is possible for the cosmetic material to have a stable quality.

In addition, since it is not necessary to dissolve the organic ultraviolet absorbent in a specific solvent, it is possible to blend the particles not only into a water-in-oil (W/O) cosmetic material but also into an aqueous cosmetic material, such as an oil-in-water (O/W) cosmetic material, skin toner or sun-screening gel, the formulation of which was difficult in the related art, and to improve the degree of freedom for the formulation of the cosmetic material.

In addition, since the average particle diameter of the composite particles is set to 0.05 µm or more and 5 µm or less, even in a case where the particles are used in a cosmetic product, there is no rough feeling or the like, and a feeling of using the product is excellent.

In addition, since the organic ultraviolet absorbent and the metal oxide particles having an average particle diameter of 0.003 µm or more and 0.1 µm or less are composited in the resin, visible light rays are not absorbed, and it is possible to maintain transparency which is emphasized in a cosmetic material.

DESCRIPTION OF EMBODIMENTS

Figure 1:
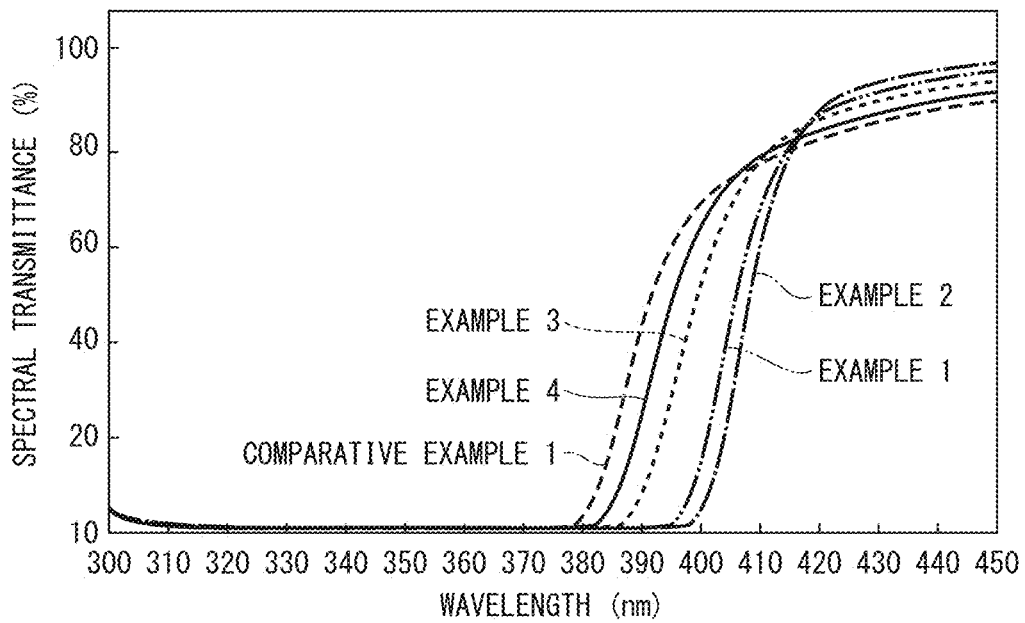
FIG. 1 is a view illustrating the spectral transmittances of respective resin monomer-dissolved liquids of Examples 1 to 4 and a resin monomer dispersion liquid of Comparative Example 1 of the invention.

Embodiments of ultraviolet-shielding composite particles, a method for manufacturing the same, an ultraviolet-shielding composite particle-containing dispersion liquid, an aqueous dispersion element, an oil-based dispersion element and a cosmetic material of the invention will be described.

Meanwhile, the following embodiments are to specifically describe the invention in order to make the purport of the invention well understood, and do not limit the invention unless particularly otherwise designated.

[Ultraviolet-Shielding Composite Particles]

Ultraviolet-shielding composite particles of the present embodiment are ultraviolet-shielding composite particles which include a resin containing an organic ultraviolet absorbent and metal oxide particles having an ultraviolet-shielding function, and have an average particle diameter of 0.05 μm or more and 5 μm or less, in which the metal oxide particles are particles which include one or two or more selected from the group consisting of zinc oxide, titanium oxide, cerium oxide and iron oxide and have an average particle diameter of 0.003 μm or more and 0.1 μm or less, a content of the organic ultraviolet absorbent in the ultraviolet-shielding composite particles is 0.1% by mass or more and 80% by mass or less, a content of the metal oxide particles is 1% by mass or more and 80% by mass or less, and the metal oxide particles are dispersed in the ultraviolet-shielding composite particles.

In a case where the ultraviolet-shielding composite particles of the embodiment are used in an aqueous cosmetic material, the metal oxide particles are preferably dispersed in the ultraviolet-shielding composite particles without being exposed on surfaces of the ultraviolet-shielding composite particles.

That is, a structure in which the metal oxide particles dispersed in the ultraviolet-shielding composite particles are in a state of being embedded and thus encapsulated in the ultraviolet-shielding composite particles is preferable.

Furthermore, a structure in which the surfaces of the ultraviolet-shielding composite particles are fully covered with the resin and the organic ultraviolet absorbent and the metal oxide particles are in a fully encapsulated state so that the metal oxide particles are not exposed on surfaces of the covered resin and organic ultraviolet absorbent is preferable.

For example, in a case where fine zinc oxide particles are used as the metal oxide particles, when the fine zinc oxide particles are embedded in the ultraviolet-shielding composite particles to be in an encapsulated state, it is possible to suppress the elution of zinc into the cosmetic material and to enhance the stable quality of the aqueous cosmetic material.

That is, in a case where the ultraviolet-shielding composite particles of the embodiment are used in the aqueous cosmetic material or the like, it is preferable that 90% by mass or more, preferably 95% by mass or more, and more preferably 99% by mass or more of the ultraviolet-shielding composite particles have the metal oxide particles that are embedded in the ultraviolet-shielding composite particles to be in an encapsulated state, and ultraviolet-shielding composite particles having a structure in which the metal oxide particles are exposed on the surfaces of the ultraviolet-shielding composite particles be not substantially included.

Meanwhile, in a case where the amount of water is small and the stable quality of a cosmetic material is not affected even when a small amount of the metal oxide particles are eluted, such as a case where the ultraviolet-shielding composite particles are used in a W/O or O/W-type cosmetic material, the metal oxide particles may not be embedded in the ultraviolet-shielding composite particles and thus not be in an encapsulated state.

The resin is not particularly limited as long as monomers of the resin can dissolve the organic ultraviolet absorbent, a polymer of the monomers has a high transparency, and the resin can be used as a raw material of the cosmetic material.

Examples of the resin monomers include those of (meth)acrylic resins, acrylic styrene copolymers, acrylic amide copolymers, acrylic epoxy copolymers, acrylic urethane copolymers, acrylic polyester copolymers, silicon acrylic copolymers, vinyl acetate resins, polyamide resins, epoxy resins, urethane resins, polyester resins, silicone resins and the like. Among the above, the monomers of the (meth)acrylic resin are preferable in terms of excellent transparency. In addition, among the above resin monomer, only one kind of monomers may be solely polymerized and used, or two or more kinds of monomers may be combined, polymerized and used.

Examples of the monomers of the (meth)acrylic resin include methyl acrylate, ethyl acrylate, propyl acrylate, n-butyl acrylate, isobutyl acrylate, hexyl acrylate, 2-ethylhexyl acrylate, n-octyl acrylate, dodecyl acrylate, lauryl acrylate, stearyl acrylate, 2-chloroethyl acrylate, phenyl acrylate, methyl α-chloroacrylate, trifluoroethyl acrylate, tetrafluoropropyl acrylate, methyl methacrylate, ethyl methacrylate, propyl methacrylate, n-butyl methacrylate, isobutyl methacrylate, hexyl methacrylate, 2-ethylhexyl methacrylate, n-octyl methacrylate, dodecyl methacrylate, lauryl methacrylate, stearyl methacrylate and the like.

In addition, examples thereof include styrene, o-methyl-styrene, m-methyl-styrene, p-methyl-styrene, α-methyl-styrene, o-ethyl-styrene, m-ethyl-styrene, p-ethyl-styrene, 2,4-dimethyl-styrene, p-n-butyl-styrene, p-t-butyl-styrene, p-n-hexyl-styrene, p-n-octyl-styrene, p-n-nonyl-styrene, p-n-decyl-styrene, p-n-dodecyl-styrene, p-methoxy-styrene, p-phenyl-styrene, p-chlorostyrene, 3,4-dichlorostyrene, vinyl acetate, vinyl propionate, vinyl benzoate, vinyl acetate, N-vinylpyrrovinyl, vinylidene fluoride, tetrafluoroethylene, hexafluoropropylene, butadiene, isoprene and the like.

Among the above monomers, only one kind of monomer may be solely polymerized, or two or more kinds of monomers may be combined and polymerized.

Meanwhile, in a case where a monomer of the (meth)acrylic resin and another monomer are combined, the content of the (meth)acrylic resin monomer is preferably 10% by mass or more and more preferably 30% by mass or more with respect to the total amount of the resin monomers from the viewpoint of transparency.

The organic ultraviolet absorbent is not particularly limited as long as the absorbent can be dissolved in the above resin monomers, and examples thereof include benzoyl methane-based compounds, benzophenone derivatives, para-aminobenzoic acid derivatives, methoxy-cinnamic acid derivatives, salicylic acid derivatives and the like. Among the above organic ultraviolet absorbents, only one kind of absorbent may be solely used, or two or more kinds of absorbents may be combined and used. Among the above, the dibenzoyl methane-based compound is preferably used.

The dibenzoyl methane-based compound is preferably alkyl alkoxy dibenzoyl methane having one or more alkyl groups and one or more alkoxy groups in a molecule.

The alkyl alkoxy dibenzoyl methane is represented by the following formula (1).

[Chem. 1]

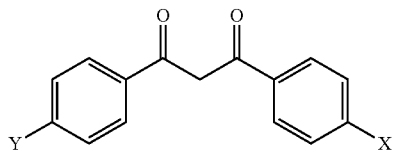

In the formula (1), X represents an alkyl group, and Y represents an alkoxy group.

Examples of the alkyl alkoxy dibenzoyl methane include 2-methyl dibenzoyl methane, 4-methyl dibenzoyl methane, 4-isopropyl dibenzoyl methane, 4-tert-butyl dibenzoyl methane, 2,4-dimethyl dibenzoyl methane, 2,5-dimethyl dibenzoyl methane, 4,4'-diisopropyl dibenzoyl methane, 4,4'-dimethoxy dibenzoyl methane, 4-tert-butyl-4'-methoxy dibenzoyl methane (avobenzone), 2-methyl-5-isopropyl-4'-methoxy dibenzoyl methane, 2-methyl-5-tert-butyl-4'-methoxy dibenzoyl methane, 2,4-dimethyl-4'-methoxy dibenzoyl methane and 2,6-dimethyl-4-tert-butyl-4'-methoxy dibenzoyl methane.

Among the above dibenzoyl methane-based compounds, 4-tert-butyl-4'-methoxy dibenzoyl methane (avobenzone) is particularly preferable in terms of ultraviolet-shielding properties and transparency.

The content of the organic ultraviolet absorbent in the composite particles is preferably 0.1% by mass or more and 80% by mass or less, more preferably 0.5% by mass or more and 50% by mass or less, and still more preferably 1% by mass or more and 30% by mass or less.

Here, when the content of the organic ultraviolet absorbent in the composite particles is less than 0.1% by mass, the amount of the organic ultraviolet absorbent is too small to sufficiently develop the ultraviolet-shielding function of the organic ultraviolet absorbent. Consequently, in order to sufficiently develop the ultraviolet-shielding function, a large amount of the composite particles are required, and material design becomes extremely difficult when producing a cosmetic material, which is not preferable. On the other hand, when the content exceeds 80% by mass, the amount of the organic ultraviolet absorbent becomes relatively large with respect to the amount of the composite particles, consequently, the dispersibility of the organic ultraviolet absorbent in the composite particles degrades, and the homogeneity of the composition is impaired, which is not preferable.

The metal oxide particles are particles which include one or two or more selected from the group consisting of zinc oxide, titanium oxide, cerium oxide and iron oxide and have an ultraviolet-shielding function, and the average particle diameter is 0.003 μm or more and 0.1 μm or less, more preferably 0.01 μm or more and 0.05 μm or less, and still more preferably 0.02 μm or more and 0.04 μm or less.

When the average particle diameter of the metal oxide particles is less than 0.003 μm, the crystallinity decreases not to develop the ultraviolet-shielding function, which is not preferable. Meanwhile, when the average particle diameter exceeds 0.1 μm, since the scattering coefficient of the particles with respect to visible light rays increases, the transparency significantly decreases, consequently, the light permeability with respect to visible light rays decreases, and the transparency deteriorates, which is not preferable.

The surfaces of the metal oxide particles to be used may have been treated using one or two or more selected from the group consisting of silica, alumina and organopolysiloxane. In a case where the surfaces of the metal oxide particles have been treated using one or two or more selected from the group consisting of silica, alumina and organopolysiloxane, it becomes difficult for the ultraviolet absorbent to be recrystallized in the resin monomers, and the stability of the resin monomer dispersion liquid over time increases, whereby the production efficiency increases, which is preferable.

The content of the metal oxide particles in the composite particles is preferably 1% by mass or more and 80% by mass or less, more preferably 10% by mass or more and 70% by mass or less, and still more preferably 20% by mass or more and 60% by mass or less.

Here, when the content of the metal oxide particles in the composite particles is less than 1% by mass, the amount of the metal oxide particles is too small to sufficiently develop the ultraviolet-shielding function of the metal oxide particles. Therefore, in order to sufficiently develop the ultraviolet-shielding function, a large amount of the composite particles are required, and material design becomes extremely difficult when producing a cosmetic material, which is not preferable. On the other hand, when the content exceeds 80% by mass, the amount of the metal oxide particles becomes relatively large with respect to the amount of the composite particles, consequently, the dispersibility of the metal oxide particles in the composite particles degrades, and the homogeneity of the composition is impaired, which is not preferable.

Furthermore, it is necessary to adjust the contents of the respective components so that the total of the contents of the respective components of the organic ultraviolet absorbent and the metal oxide particles becomes 1.1% by mass or more and 80% by mass or less.

In a case where the total of the respective components is less than 1.1% by mass, the amount of an ultraviolet-shielding agent is too small to sufficiently develop the ultraviolet-shielding function. On the other hand, when the total of the respective components exceeds 80% by mass, the amount of the organic ultraviolet absorbent and the metal oxide particles becomes relatively large with respect to the composite particles, consequently, the dispersibility of the metal oxide particles in the composite particles degrades, and the homogeneity of the composition is impaired, which is not preferable.

The organic ultraviolet absorbent and the metal oxide particles may be appropriately combined and used in consideration of wavelength regions in which the respective materials can be absorbed or shielded.

For example, zinc oxide is an n-type metal oxide semiconductor, and has a band gap energy Eg of 3.2 eV in the band structure. Therefore, when light having energy that is the band gap energy Eg or more is radiated on the zinc oxide, electrons absorb the light energy and are excited to the conduction band from the valence band. Since the absorption end of zinc oxide is approximately 380 nm, zinc oxide can absorb in the wavelength region from long-wavelength ultraviolet light (UVA) to middle-wavelength ultraviolet light (UVB). Considering the above fact, an organic ultraviolet absorbent that can shield long-wavelength ultraviolet light (UVA) and an organic ultraviolet absorbent that can shield middle-wavelength ultraviolet light (UVB) are preferably combined and used.

In addition, while titanium oxide has a band gap energy Eg of 3.0 eV to 3.2 eV in the band structure, since electrons are excited through indirect transition in titanium oxide, the absorption of light begins from approximately 320 nm, which is a much lower wavelength than an absorption wavelength assumed from the value of the energy band gap. Therefore, titanium oxide has a strong effect of shielding in the wavelength region of middle-wavelength ultraviolet light (UVB), and is preferably combined and used with an organic ultraviolet absorbent that can shield long-wavelength ultraviolet light (UVA).

Examples of the combination of the organic ultraviolet absorbent and the metal oxide particles include a combination of zinc oxide that can shield in the wavelength region of 380 nm or lower and a dibenzoyl methane-based compound having a maximum absorption of 358 nm to 360 nm.

In a case where zinc oxide and the dibenzoyl methane-based compound are simply mixed with the monomers, the ultraviolet-shielding function is developed from a wavelength area of 400 nm or lower as described in Examples 1 and 2 below. Meanwhile, in a case where zinc oxide and a dibenzoyl methane-based compound are made into composite particles, the ultraviolet-shielding function is developed from approximately 410 nm although the absolute amount of zinc oxide and the dibenzoyl methane-based compound is small compared with Examples 1 and 2, as described in Examples 6 and 7 below.

The reasons for developing the above effect are considered to be as follows.

That is, in a case where light transmits through the composite particles, since light is scattered or reflected by the metal oxide particles in the composite particles while traveling, light travels a longer distance compared with a case where light transmits through resin particles including no metal oxide particles. Therefore, it is considered that, in a case where the metal oxide particles and the organic ultraviolet absorbent are combined and mixed, the time for the organic ultraviolet absorbent in the composite particles to be in contact with light increases compared with a case where the organic ultraviolet absorbent is solely mixed in, and the absorption effect also increases.

Furthermore, it is considered that, when the composite particles are produced by dispersing the metal oxide particles and the organic ultraviolet absorbent in the resin, the metal oxide particles and the organic ultraviolet absorbent come close to each other in a narrow range of an average particle diameter of 0.05 μm or more and 5 μm or less, and therefore the scattering and reflection by the metal oxide and the absorption of the organic ultraviolet absorbent are repeated more frequently, thereby obtaining the effect.

The dispersed particle diameter of the metal oxide particles in the composite particles is preferably 0.1 μm or less, more preferably 0.05 μm or less, and still more preferably 0.03 μm or less.

Here, when the dispersed particle diameter of the metal oxide particles in the composite particles exceeds 0.1 μm, the scattering coefficient of the composite particles with respect to visible light rays increases, the transparency significantly decreases, consequently, the transparency decreases, and there is a concern of loss of clarity depending on the cases, which is not preferable.

The average particle diameter of the composite particles is 0.05 μm or more and 5 μm or less, more preferably 0.1 μm or more and 3 μm or less, and still more preferably 0.2 μm or more and 1 μm or less.

Here, when the average particle diameter of the composite particles is less than 0.05 μm, it becomes difficult to disperse the metal oxide particles having an average particle diameter of 0.003 μm or more and 0.1 μm or less and an ultraviolet-shielding function in the resin without exposing the metal oxide particles on the surfaces of the composite particles, which is not preferable. Meanwhile, when the average particle diameter exceeds 5 μm, in a case where the composite particles are used as a cosmetic material, the spreading or sliding properties of the cosmetic material on skin degrade, and, consequently, a rough feeling or the like is caused to deteriorate a sense of touch or the like, which deteriorates a feeling of using the product, which is not preferable.

Here, the average particle diameter of the ultraviolet-shielding composite particles refers to the diameter of particles at the 50 volume % (D50) in a cumulative volume particle size distribution which is obtained by producing a dispersion liquid by dispersing 5% by mass of the ultraviolet-shielding composite particles, 10% by mass of polyester-modified silicone and 85% by mass of decamethyl cyclopentasiloxane SH245 (manufactured by Dow Corning Toray Co., Ltd.) using a sand mill through 2500 times of rotation for 3 hours, and measuring the dispersed particle diameters using a dynamic light scattering nanoparticle size analyzer LB-550 (manufactured by Horiba, Ltd.).

Meanwhile, the dispersed particle diameter of D50 obtained using the above measurement method almost coincides with the diameter of the primary particle of the resin particles when observing the ultraviolet-shielding composite particles using a scanning electron microscope. Therefore, the average primary particle diameter of the ultraviolet-shielding composite particles may be measured as the average particle diameter of the ultraviolet-shielding composite particles.

The surfaces of the composite particles may be treated using 1% by mass or more and 20% by mass or less of organosiloxane with respect to the composite particles as necessary.

Examples of the organosiloxane include dialkyl alkoxy silane compounds, and, among the above, organopolysiloxane or modified organopolysiloxane obtained by modifying organopolysiloxane using one or two or more selected from the group consisting of alkyl groups, isocyanate groups, epoxy groups, acryl groups and alkyl-silicon compounds is preferably used. Particularly, dimethyl polysiloxane (silicone oil) and modified dimethyl polysiloxane (modified silicone oil) obtained by modifying the dimethyl polysiloxane (silicone oil) are preferably used.

When the surfaces of the composite particles are treated using organosiloxane, it is possible to further suppress the elution of the metal oxide, which is a component of the composite particles, into a solvent, such as pure water.

[Method for Manufacturing the Ultraviolet-Shielding Composite Particles]

There are two methods for manufacturing the ultraviolet-shielding composite particles of the embodiment.

(1) A method for manufacturing ultraviolet-shielding composite particles, in which metal oxide particles having an average particle diameter of 0.003 μm or more and 0.1 μm or less and an ultraviolet-shielding function are dispersed in 1% by mass or more and 50% by mass or less of dispersant-containing resin monomers with respect to the metal oxide particles to produce a resin monomer dispersion liquid containing the metal oxide particles, then, 0.1% by mass or more and 80% by mass or less of an organic ultraviolet absorbent is dissolved in the resin monomer dispersion liquid to produce a resin monomer-dissolved liquid containing the metal oxide particles and the organic ultraviolet-shielding absorbent, then, the resin monomer-dissolved liquid is suspended or emulsified in pure water including a suspension protectant, a silicone-based defoamer and a crosslinking agent to produce a suspended liquid or an emulsified liquid, and then a polymerization initiator is added to the suspended liquid or the emulsified liquid to perform suspension polymerization or emulsion polymerization, thereby generating ultraviolet-shielding composite particles.

(2) A method for manufacturing ultraviolet-shielding composite particles, in which 0.1% by mass or more and 80% by mass or less of an organic ultraviolet absorbent is dissolved to produce a resin monomer-dissolved liquid containing the organic ultraviolet absorbent, then, 1% by mass or more and 80% by mass or less of metal oxide particles having an average particle diameter of 0.003 μm or more and 0.1 μm or less and an ultraviolet-shielding function are dispersed in the resin monomer-dissolved liquid to produce a resin monomer dispersion liquid containing the metal oxide particles and the organic ultraviolet absorbent, then, the resin monomer dispersion liquid is suspended or emulsified in pure water including a suspension protectant, a silicone-based defoamer and a crosslinking agent to produce a suspended liquid or an emulsified liquid, and then a polymerization initiator is added to the suspended liquid or the emulsified liquid to perform suspension polymerization or emulsion polymerization, thereby generating ultraviolet-shielding composite particles.

Here, the above method (1) will be first described.

First, metal oxide particles having an average particle diameter of 0.003 μm or more and 0.1 μm or less and an ultraviolet-shielding function are dispersed in dispersant-containing resin monomers to produce a resin monomer dispersion liquid containing the metal oxide particles.

The dispersant preferably has a high affinity to the resin monomers and a high hydrophobicity. That is, the dispersant covers the metal oxide particles to promote dispersion with respect to the resin monomers, simultaneously, almost all particles of the metal oxide are brought into a monodisperse state within a relative short period of time, and the average dispersed particle diameter becomes 0.003 μm or more and 0.1 μm or less.

In addition, since the dispersant supplies hydrophobicity to the metal oxide particles, the metal oxide particles do not separate from the polymer, and the dispersant helps the metal oxide particles to be embedded in the resin without migrating into a water phase.

Examples of the dispersant include carboxylic acids, such as sodium carboxymethyl cellulose, or salts thereof, sulfonic acids, such as sodium alkane sulfonic acids, or salts thereof, sulfuric acid esters, such as sodium polyoxyethylene nonyl phenyl ether sulfate, or salts thereof, phosphoric acid esters, such as polyoxyethylene alkyl phenyl ether phosphoric acid and polyoxyethylene alkyl ether phosphoric acid, or salts thereof, and phosphonic acids, such as sodium lauryl phosphonic acid, or salts thereof. Among the above, phosphoric acid esters or salts thereof are preferable.

Particularly, in a case where the ultraviolet-shielding composite particles of the embodiment are used in a cosmetic material, the dispersant should be recognized as a raw material of the cosmetic material at the same time.

The addition rate of the dispersant with respect to the metal oxide particles is preferably 1% by mass or more and 50% by mass or less. When the addition rate is less than 1% by mass, the amount of the dispersant is too small to cover the surfaces of the metal oxide particles and to obtain a sufficiently dispersed state of the metal oxide particles. On the other hand, when the addition rate exceeds 50% by mass, the dispersibility cannot be further improved even by increasing the addition rate more, and the dispersant is wasted.

A dispersing device being used is not particularly limited as long as a sufficient dispersion energy is supplied to a dispersion system, and examples thereof include a ball mill, a sand mill, an ultrasonic dispersing device, a homogenizer and the like.

The dispersing time is preferably approximately 30 minutes to 3 hours, but an appropriate time may be selected in consideration of both the dispersion state and the manufacturing cost.

Thereby, a resin monomer dispersion liquid having the metal oxide particles of an average dispersed particle diameter of 0.003 μm or more and 0.1 μm or less can be obtained.

Next, when the above organic ultraviolet absorbent is dissolved in the resin monomer dispersion liquid so as to become 0.1% by mass or more and 80% by mass or less in the resin monomer dispersion liquid, a resin monomer-dissolved liquid containing the metal oxide particles and the organic ultraviolet absorbent can be obtained.

The dissolving method is not particularly limited, an appropriate mixing method may be selected in consideration of the compatibility of the resin monomer dispersion liquid and the organic ultraviolet absorbent, and, for example, the organic ultraviolet absorbent is mixed until the sedimentation of a solid content cannot be visually confirmed. As mixing means, for example, a magnetic stirrer, a stirrer or the like can be used.

Next, the resin monomer-dissolved liquid is suspended or emulsified in pure water including a suspension protectant, a silicone-based defoamer and a crosslinking agent to produce a suspended liquid or an emulsified liquid having a dispersed particle diameter of 0.05 µm to 5 µm.

Examples of the suspension protectant include non-ionic surfactants, such as polyoxyethylene alkyl ethers and polyoxy ethylene alkyl phenyl ethers, anionic surfactants, such as alkyl benzene sulfonic acid salts, alkyl sulfuric acid ester salts and alkyl phenyl sulfuric acid esters, and the like, and, among the above, the anionic surfactants are preferable, and the anionic surfactant is preferably an alkyl benzene sulfonic acid salt.

The addition amount of the above suspension protectant is 0.1% by mass or more and 10% by mass or less, and more preferably 0.1% by mass or more and 2% by mass or less with respect to the resin monomer-dissolved liquid.

Examples of the silicone-based defoamer include oil-type defoamers, oil compound-type defoamers, solution-type defoamers, powder-type defoamers, solid-type defoamers, emulsion-type defoamers, self-emulsification-type defoamers and the like, and, among the above, the oil compound-type defoamers are preferable.

The addition amount of the silicone-based defoamer is preferably 0.01% by mass or more and 5% by mass or less and more preferably 0.1% by mass or more and 1% by mass or less with respect to the above resin monomer-dissolved liquid.

When 0.01% by mass or more and 5% by mass or less of the silicone-based defoamer is added with respect to the above resin monomer-dissolved liquid, the stirring rate of a mixer, a stirrer, a homomixer, a homogenizer or the like can be significantly increased, and the composite particles can be miniaturized to approximately 50 nm. As a result, when the composite particles are blended into a cosmetic material or the like, a cosmetic material having superior transparency and an excellent feeling of using the product such as free of a rough feeling, can be provided. In addition, the stirring rate of a mixer, a stirrer, a homomixer, a homogenizer or the like can be significantly increased, and, consequently, it is possible to improve the manufacturing efficiency of the ultraviolet-shielding composite particles, and therefore the manufacturing cost can be significantly reduced.

The crosslinking agent is not particularly limited as long as the crosslinking agent is a monomer having two or more unsaturated double bonds, and can be appropriately selected from polyfunctional vinyl monomers, polyfunctional (meth) acrylic acid ester derivatives and the like.

More specific examples thereof include (poly) alkylene glycol-based di(meth)acrylates, such as divinyl benzene, divinyl biphenyl, divinyl naphthalene, (poly) ethylene glycol di(meth)acrylate, (poly) propylene glycol di(meth)acrylate and (poly)tetramethylene glycol di(meth)acrylate.

In addition, examples thereof include alkanediol-based di(meth)acrylates, such as 1,6-hexanediol di(meth)acrylate, 1,8-octanediol di(meth)acrylate, 1,9-nonanediol di(meth) acrylate, 1,10-decanediol di(meth)acrylate, 1,12-dodecandiol di(meth)acrylate, 3-methyl-1,5-pentanediol di(meth) acrylate, 2,4-diethyl-1,5-pentanediol di(meth)acrylate, butyl ethyl propanediol di(meth)acrylate, 3-methyl-1,7-octanediol di(meth)acrylate and 2-methyl-1,8-octanediol di(meth)acrylate.

In addition, examples thereof include neopentyl glycol di(meth)acrylates, trimethylol-propane tri(meth)acrylates, tetramethylol-methane tri(meth)acrylates, tetramethylol-propane tetra(meth)acrylates, pentaerythritol tri(meth)acrylates, ethoxified cyclohexane dimethanol di(meth)acrylates, ethoxified bisphenol A di(meth)acrylates, tricyclo-decane dimethanol di(meth)acrylates, propoxified ethoxified bisphenol A di(meth)acrylates, 1,1,1-tris hydroxyl-methyl ethane di(meth)acrylates, 1,1,1-tris hydroxyl methyl ethane tri (meth)acrylates, 1,1,1-tris hydroxyl methyl propane triacrylates, diaryl phthalates and isomers thereof, triaryl isocyanuate and derivatives thereof, and the like.

Among the above, (poly) ethylene glycol di(meth)acrylates are particularly preferable.

The addition amount of the crosslinking agent is preferably 0.1% by mass or more and 10% by mass or less, and more preferably 1% by mass or more and 10% by mass or less with respect to the above resin monomer-dissolved liquid.

Next, a polymerization initiator is added to the above suspended liquid or the emulsified liquid, and suspension polymerization or emulsion polymerization is performed.

Examples of the polymerization initiator include salts of persulfuric acid, such as potassium persulfate and ammonium persulfate; organic peroxides, such as hydrogen peroxide, benzoyl peroxide, lauroyl peroxide, t-butyl hydroperoxide, benzoyl peroxide and cumene hydroperoxide; azo-based polymerization initiators, such as azobisdiisobutyronitrile and 2,2-azobis(2-amidinopropane) dihydrochloride; and the like, and, among the above, the salts of persulfuric acid are preferable.

The addition amount of the polymerization initiator is preferably 0.01% by mass or more and 1% by mass or less and more preferably 0.05% by mass or more and 0.5% by mass or less with respect to the above resin monomer-dissolved liquid.

In the polymerization method, polymerization is preferably initiated by stirring and heating the above suspended liquid or the emulsified liquid in a nitrogen atmosphere and in the presence of the polymerization initiator.

The polymerization initiating temperature is preferably set to 50° C. to 80° C. In addition, the time of polymerizing the liquid while holding the above temperature is preferably approximately 1 hour to 5 hours, and an appropriate time may be selected in consideration of a period of time, during which the amount of unreacted residual monomers becomes the minimum, the polymerization state and the manufacturing cost.

After that, the liquid is cooled using ice or naturally cooled, and the polymerization reaction is stopped.

When the content of the suspension protectant, the silicone-based defoamer and the polymerization initiator is limited to the above range, it is possible to control the average particle diameter of the obtained ultraviolet-shielding composite particles to 0.05 µm or more and 5 µm or less.

Next, in order to remove the residual monomers, polymerization initiator and surfactant from the obtained polymer, the polymer is sufficiently washed using an alcohol, and then washed using pure water.

The alcohol is preferably an alcohol that is soluble in pure water and is easily washed away, examples thereof include ethanol, 2-propanol and the like, and 2-propanol is particularly preferable.

The washing method is not particularly limited as long as the residual monomers and the like can be removed, and the polymer is washed using pressure filtration, suction filtration, a filter press, centrifugal separation, ultrafiltration, decantation or the like. For example, in a case where the polymer is washed using 2-propanol, washing is carried out until the concentration of 2-propanol becomes 1% or less, and the conductivity becomes 20 µS/cm or less.

After the completion of the washing, the obtained polymer is dried at 80° C. to 100° C. to remove the alcohol or the pure water, and then the obtained polymer is ground. The drying method is not particularly limited as long as the alcohol or the pure water can be removed, and examples thereof include drying at atmospheric pressure, drying in a vacuum and the like.

The grinding method is not particularly limited as long as the respective particles having an average particle diameter of 0.05 μm or more and 5 μm or less can be cracked, and examples thereof include with a pin mill, a hammer mill, a jet mill, an impeller mill and the like.

The ultraviolet-shielding composite particles can be generated using the above method (1).

When the respective particles agglomerated by the drying are ground by the ultraviolet-shielding composite particles going through a grinding process, it is possible to improve a feeling of using the product in a case where the particles are used in a cosmetic material.

Next, the above method (2) will be described.

First, 0.1% by mass or more and 80% by mass or less of an organic ultraviolet absorbent is dissolved in a resin monomer to produce a resin monomer-dissolved liquid containing the organic ultraviolet absorbent.

As the organic ultraviolet absorbent and the resin monomers, the previously described organic ultraviolet absorbent and resin monomers are preferably used.

Next, 1% by mass or more and 80% by mass or less of metal oxide particles having an average particle diameter of 0.003 μm or more and 0.1 μm or less and an ultraviolet-shielding function are dispersed in the resin monomer-dissolved liquid to produce a resin monomer dispersion liquid containing the metal oxide particles and the organic ultraviolet absorbent.

As the metal oxide particles, the previously described metal oxide particles are preferably used.

In addition, 1% by mass or more and 50% by mass or less of the previously described dispersant with respect to the metal oxide particles may be included and dispersed in the resin monomer dispersion liquid.

Next, the resin monomer dispersion liquid is suspended or emulsified in pure water including a suspension protectant, a silicone-based defoamer and a crosslinking agent to produce a suspended liquid or an emulsified liquid having a dispersed particle diameter of 0.05 μm to 5 μm.

The flow from the process of making the resin monomer dispersion liquid into the suspended liquid or the emulsified liquid to the process of adding the polymerization initiator to the suspended liquid or the emulsified liquid to perform suspension polymerization and emulsion polymerization, thereby generating the ultraviolet-shielding composite particles is completely the same as that in the above method (1), and thus will not be described.

The ultraviolet-shielding composite particles can also be generated using the above method (2).

When the respective particles agglomerated by the drying are ground by the ultraviolet-shielding composite particles going through a grinding process, it is possible to improve a feeling of using the product in a case where the particles are used in a cosmetic material.

[Ultraviolet-Shielding Composite Particle-Containing Dispersion Liquid]

The ultraviolet-shielding composite particle-containing dispersion liquid of the embodiment is a dispersion liquid, in which the above ultraviolet-shielding composite particles are dispersed in a dispersion medium, and the content of the ultraviolet-shielding composite particles is 1% by mass or more and 80% by mass or less, more preferably 20% by mass or more and 70% by mass or less, and still more preferably 30% by mass or more and 60% by mass or less.

The dispersion medium is not limited as long as the dispersion medium can disperse the above ultraviolet-shielding composite particles, and examples thereof that can be preferably used include, in addition to water, alcohols, such as methanol, ethanol, 2-propanol, butanol and octanol; esters, such as ethyl acetate, butyl acetate, ethyl lactate, propylene glycol monomethyl ether acetate, propylene glycol monoethyl ether acetate and γ-butyrolactone; ethers, such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether and diethylene glycol monoethyl ether; ketones, such as acetone, methyl ethyl ketone, methyl isobutyl ketone, acetyl-acetone and cyclohexanone; aromatic hydrocarbons, such as benzene, toluene, xylene and ethylbenzene; amides, such as dimethyl formamide, N,N-dimethyl aceteamide and N-methyl-pyrrolidone; chain-like polysiloxanes, such as dimethylpolysiloxane, methyl phenyl polysiloxane and diphenyl polysiloxane; cyclic polysiloxanes, such as octamethyl cyclotetrasiloxane, decamethylcyclopentasiloxane and dodecamethylcyclohexanesiloxane; modified polysiloxanes, such as amino-modified polysiloxane, polyether-modified polysiloxane, alkyl-modified polysiloxane and fluorine-modified polysiloxane. Only one of the above solvents or a mixture of two or more can be used.

Here, when the content of the ultraviolet-shielding composite particles is less than 1% by mass, the amount of the organic ultraviolet absorbent becomes too small for the dispersion liquid to sufficiently develop the ultraviolet-shielding function, and, consequently, material design becomes extremely difficult when producing a cosmetic material, which is not preferable. On the other hand, when the content exceeds 80% by mass, the amount of the organic ultraviolet absorbent in the dispersion liquid is relatively large, consequently, the dispersibility of the organic ultraviolet absorbent in the dispersion liquid decreases, and the homogeneity of the composition is impaired, which is not preferable.

The dispersion liquid can be obtained by mixing the above ultraviolet-shielding composite particles with the dispersion medium, mixing the dispersant or a water-soluble binder as necessary, then, performing a dispersion treatment on the mixture using a disperser or a mixer, such as a beads mill, a ball mill or a homogenizer in which a sand mill and zirconia beads are used, and dispersing the ultraviolet-shielding composite particles in the dispersion medium.

In addition, the necessary time for the dispersion treatment is not particularly limited as long as the time is long enough for the ultraviolet-shielding composite particles to be dispersed in the dispersion medium.

[Ultraviolet-Shielding Composite Particle-Containing Aqueous Dispersion Element]

The ultraviolet-shielding composite particle-containing aqueous dispersion element of the embodiment is an ultraviolet-shielding composite particle-containing aqueous dispersion element, in which the above ultraviolet-shielding composite particles are dispersed in a dispersion medium including alcohols, and is an aqueous dispersion element including 1% by mass or more and 80% by mass or less, more preferably 20% by mass or more and 70% by mass or less, and furthermore preferably 30% by mass or more and 60% by mass or less of the ultraviolet-shielding composite particles and 5% by mass or more and 20% by mass or less of the alcohol.

The aqueous dispersion element may further contain 0.001% by mass to 10% by mass, more preferably 0.005% by mass to 5% by mass and furthermore preferably 0.01% by mass to 3% by mass of a water-soluble macromolecule. In this case, it is necessary to adjust the contents of the respective components so that the total of the contents of the respective components of the ultraviolet-shielding composite particles, the alcohol and the aqueous macromolecule does not exceed 100% by mass.

Examples of the alcohol include monovalent alcohols or polyvalent alcohols having 1 to 6 carbon atoms, such as ethanol, 1-propanol, 2-propanol, 1-butanol, 2-butanol, glycerin, 1,3-butylene glycol, propylene glycol and sorbitol, and, among the above, a monovalent alcohol, particularly, ethanol is preferable.

In a case where the aqueous dispersion element does not include the water-soluble macromolecule, the content of the alcohol is preferably 5% by mass or more and 20% by mass or less, and more preferably 10% by mass or more and 20% by mass or less.

Particularly, in a case where the content of the alcohol is set to 10% by mass or more and 20% by mass or less, it is possible to improve the dispersibility and stability of the ultraviolet-shielding composite particles in the aqueous dispersion element over time.

In addition, in a case where the aqueous dispersion element includes the water-soluble macromolecule, the water-soluble macromolecule is not particularly limited as long as the aqueous macromolecule can be used for a cosmetic product, and examples thereof include gum arabic, sodium alginate, casein, carrageenan, galactan, carboxyvinyl polymers, carboxymethyl cellulose, sodium carboxymethyl cellulose, carboxymethyl starch, agar, xanthan gum, quince seed, guar gum, collagen, gelatin, cellulose, dextran, dextrin, tragacanth gum, hydroxyl ethyl cellulose, hydroxyl propyl cellulose, sodium hyaluronate pectin, pullulan, methyl cellulose, methyl hydroxypropyl cellulose and the like. Only one of the water-soluble macromolecules may be solely used, or a mixture of two or more may be used.

The water-soluble macromolecule plays a role as the dispersant and a viscosity adjuster, and the addition improves the dispersibility and stability of the ultraviolet-shielding composite particles in the aqueous dispersion element over time.

In a case where the aqueous dispersion element includes the water-soluble macromolecule, the content of the alcohol is preferably 5% by mass or more and 20% by mass or less, and more preferably 15% by mass or more and 20% by mass or less.

Here, the reason why the content of the alcohol, in a case where the aqueous dispersion element includes the water-soluble macromolecule, is set to 5% by mass or more and 20% by mass or less, is that, when the content is less than 5% by mass, the content of the alcohol is too small, therefore, the water-soluble macromolecule cannot evenly infiltrate into the alcohol and unevenly swells due to moisture, consequently, the dispersibility of the ultraviolet-shielding composite particles decreases to be difficult for handling, and, furthermore, the stability of the aqueous dispersion element over time degrades, which is not preferable. In addition, when the content exceeds 20% by mass, the viscosity of the entire aqueous dispersion element becomes high, the dispersion stability of the ultraviolet-shielding composite particles degrades, and the stability of the aqueous dispersion element over time also degrades, which is not preferable.

The ultraviolet-shielding composite particle-containing aqueous dispersion element can be obtained by mixing the above ultraviolet-shielding composite particles with a solvent (dispersion medium) including the alcohol or a mixture (dispersion medium) including the alcohol and the water-soluble macromolecule, then mixing water, and dispersing the particles. The amount of water may be appropriately adjusted, and is preferably adjusted in a range of 15% by mass or more and 94% by mass or less. When the amount of water is adjusted in the above range, it is possible to obtain an ultraviolet-shielding composite particle-containing aqueous dispersion element that can ensure sufficient transparency in a case where the dispersion element is spread and coated on skin.

The mixing method is not particularly limited, and the ultraviolet-shielding composite particle-containing aqueous dispersion element can be obtained by performing a dispersion treatment using a disperser or a mixer, such as a beads mill, a ball mill or a homogenizer in which a sand mill and zirconia beads are used, and dispersing the ultraviolet-shielding composite particles in the dispersion medium.

In addition, the necessary time for the dispersion treatment is not particularly limited as long as the time is long enough for the ultraviolet-shielding composite particles to be dispersed in the dispersion medium.

[Ultraviolet-Shielding Composite Particle-Containing Oil-Based Dispersion Element]

The ultraviolet-shielding composite particle-containing oil-based dispersion element of the embodiment is an ultraviolet-shielding composite particle-containing oil-based dispersion element, in which the above ultraviolet-shielding composite particles are dispersed in an oily component including a surfactant, and is an oil-based dispersion element including 1% by mass or more and 80% by mass or less, more preferably 20% by mass or more and 70% by mass or less, and furthermore preferably 30% by mass or more 60% by mass and less of the ultraviolet-shielding composite particles and 1% by mass or more and 40% by mass or less of the surfactant with respect to the ultraviolet-shielding composite particles.

The oily component is not particularly limited as long as the component can be used for a cosmetic product, and examples thereof include hydrocarbons, fatty oils, waxes, hardened oils, ester oils, aliphatic acids, higher alcohols, silicone oils, fluorine-based oils, lanoline derivatives, oily gelators and the like. The oily component may be derived from any of animal oils, plant oils, synthetic oils and the like, and may have any properties of solid oils, semisolid oils, liquid oils, volatile oils and the like.

Examples of the hydrocarbons include liquid paraffins, squalene, Vaseline, polyethylene waxes, ethylene-propylene copolymers, paraffin waxes, montan waxes, Fischer-Tropsch waxes, polyisobutylene, polybutene, ceresin waxes, ozokerite waxes and the like.

Examples of the fatty oils include Japan waxes, olive oil, castor oil, mink oil, macadamia oil and the like.

Examples of the waxes include beeswax, spermaceti, Carnauba wax, candelilla wax and the like.

Examples of the ester oils include jojoba oil, glyceryl trioctanoin acid, polyglyceryl diisostearic acid, diclyceryl triisostearic acid, glyceryl tribehenate, cetyl 2-ethylhexanoic acid, isopropyl myristate, isopropyl palmitate, octyl-dodecyl myritate, pentaerythrityl ester rosinate, neopentyl glycol dioctanoate, cholesterol fatty acid ester, phytosterol fatty acid esters, triglycerides, diisostearyl malate and the like.

Examples of the aliphatic acids include stearic acid, lauric acid, myristic acid, behenic acid, isostearic acid, oleic acid and the like.

Examples of the higher alcohols include stearyl alcohol, cetyl alcohol, lauryl alcohol, oleyl alcohol, isostearyl alcohol, behenyl alcohol and the like.

Examples of the silicone oils include chain-like silicone, such as dimethyl polysiloxane and methyl phenyl polysiloxane; cyclic silicone, such as octamethylcyclotetrasiloxane and decamethylcyclopentasiloxane; modified silicone, such as crosslinking polyether-modified methyl polysiloxane, methacryl-modified organopolysiloxane, stearyl-modified organopolysiloxane, oleyl-modified organopolysiloxane, behenyl-modified organopolysiloxane, alkoxy-modified organopolysiloxane, fluorine-modified organopolysiloxane, fluorine-modified polysiloxane, amino-modified polysiloxane, fatty acid-modified polysiloxane and higher alcohol-modified polysiloxane; methyl phenyl polysiloxane having a high degree of polymerization, dimethyl polysiloxane having a high degree of polymerization, crosslinking organopolysiloxane and the like.

Only one of the silicone oils may be solely used, or a mixture of two or more may be used.

Among the above silicone oils, a chain-like silicone having a low molecular weight of 20000 or less or a volatile silicone is preferable since the silicone has a low surface tension and is thus smoothly spread when coated on skin. In addition, since the silicone oils have a smooth feeling, a sticky feeling or oiliness is reduced, and a fresh feeling of using a cosmetic product can be obtained, which is preferable.

Examples of the fluorine-based oils include perfluorodecane, perfluorooctane, perfluoropolyether and the like.

Examples of the lanoline derivatives include lanoline, lanoline acetate, lanoline fatty acid isopropyl ester, lanoline alcohols and the like.

Examples of the oily gelators include sucrose fatty acid ester, starch fatty acid ester, aluminum isostearate, 1,2-hydroxy-stearic acid and the like.

Only one of the above oily components may be solely used or a mixture of two or more may be used.

Among the above oily components, the silicone oil is preferable since the silicone oil reduces a sticky feeling or oiliness, and a fresh feeling of using the product can be obtained.

The surfactant is not particularly limited as long as the surfactant can be used for cosmetic products, and examples thereof include non-ionic surfactants, anionic surfactants, cationic surfactants, ampholytic surfactants and the like.

Examples of the non-ionic surfactants include glycerin fatty acid esters and alkylene glycol adducts thereof, polyglycerin fatty acid esters and alkylene glycol adducts thereof, propylene glycol fatty acid esters and alkylene glycol adducts, sorbitan fatty acid esters and alkylene glycol adducts thereof, fatty acid esters of sorbitol and alkylene glycol adducts thereof, polyalkylene glycol fatty acid esters, sucrose fatty acid esters, polyoxyl alkylene alkyl esters, glycerine alkyl ethers, polyoxyethylene alkyl phenyl ethers, polyoxyethylene cured castor oil, alkylene glycol adducts of lanoline, poloxyalkylene alkyl-comodified silicone, polyether-modified silicone and the like.

Examples of the anionic surfactants include inorganic and organic salts of fatty acids, such as stearic acid and lauric acid, alkyl benzene sulfate, alkyl sulfonate, α-olefin sulfonate, dialkyl sulfosuccinate, α-sulfonated fatty acid salts, acyl methyl taurate, N-methyl-N-alkyl taurate, polyoxy-ethylene alkyl ether sulfate, polyoxy-ethylene alkyl phenyl ether sulfate, alkyl phosphate, polyoxy-ethylene alkyl ether phosphate, polyoxy-ethylene alkyl phenyl ether phosphate, N-acyl aminoate, N-acyl-N-alkyl aminoate, o-alkyl-substituted malate, alkyl sulfosuccinate and the like.

Examples of the cationic surfactants include alkyl amine salts, polyamine and alkanolamine fatty acid derivatives, alkyl quaternary ammonium salts, cyclic quaternary ammonium salts, and the like.

Examples of the ampholytic surfactants include carbonic acid-type surfactants, sulfate surfactants, sulfonate surfactants, phosphate surfactants and the like.

Only one of the above surfactants may be solely used, or a mixture of two or more may be used. Among the surfactants, a non-ionic surfactant is preferable, and, in particular, polyether-modified silicone is preferable since the dispersibility is favorable, and it is possible to obtain a cosmetic material having excellent adhesion to skin.

The content of the surfactant in the oil-based dispersion element is preferably 1% by mass or more and 40% by mass or less, and more preferably 10% by mass or more and 30% by mass or less with respect to the ultraviolet-shielding composite particles.

Here, the reason why the content of the surfactant in the oil-based dispersion element is set to 1% by mass or more and 40% by mass or less is that, when the content is less than 1% by mass, since the content of the surfactant is too small, the surfactant cannot evenly infiltrate onto the surfaces of the ultraviolet-shielding composite particles, consequently, the dispersibility of the ultraviolet-shielding composite particles degrades to be difficult for handling, and, furthermore, the stability of the oil-based dispersion element over time degrades, which is not preferable. In addition, when the content exceeds 40% by mass, the viscosity of the entire oil-based dispersion element is high, the dispersion stability of the ultraviolet-shielding composite particles degrades, the stability of the oil-based dispersion element over time degrades, and a sticky feeling or oiliness increases, which is not preferable.

The ultraviolet-shielding composite particle-containing oil-based dispersion element can be obtained by mixing the above ultraviolet-shielding composite particles with a mixture (dispersion medium) including a solvent (dispersion medium) including the oily component and the surfactant. The amount of the oily component may be appropriately adjusted, and is preferably adjusted in a range of 10% by mass or more and 90% by mass or less.

When the amount of the oily component is adjusted in the above range, it is possible to obtain an ultraviolet-shielding composite particle-containing oil-based dispersion element that can ensure sufficient transparency in a case where the dispersion element is spread and coated on skin.

The mixing method is not particularly limited, and the ultraviolet-shielding composite particle-containing oil-based dispersion element can be obtained by performing a dispersion treatment using a disperser or a mixer, such as a beads mill, a ball mill or a homogenizer in which a sand mill and zirconia beads are used, and dispersing the ultraviolet-shielding composite particles in the dispersion medium.

In addition, the necessary time for the dispersion treatment is not particularly limited as long as the time is long enough for the ultraviolet-shielding composite particles to be dispersed in the dispersion medium.

[Cosmetic Material]

The cosmetic material of the embodiment is a cosmetic material including 1% by mass or more and 60% by mass or less of one or two or more selected from the group consisting of the ultraviolet-shielding composite particles, the ultraviolet-shielding composite particle-containing dispersion liquid, the ultraviolet-shielding composite particle-containing aqueous dispersion element and the ultraviolet-shielding composite particle-containing oil-based dispersion element in terms of the ultraviolet-shielding composite particles, and, when the cosmetic material contains the ultraviolet-shielding composite particles in the above range, there is no concern of white cast, sufficient transparency can be ensured, furthermore, there is no rough feeling, and a feeling of using the product becomes excellent.

The cosmetic material can be obtained by blending one or two or more selected from the group consisting of the ultraviolet-shielding composite particles, the ultraviolet-shielding composite particle-containing dispersion liquid, the ultraviolet-shielding composite particle-containing aqueous dispersion element and the ultraviolet-shielding composite particle-containing oil-based dispersion element into a milky liquid, a cream, a foundation, a lip stick, a blush, an eye shadow or the like as blended in the related art.

Furthermore, when one or two or more selected from the group consisting of the ultraviolet-shielding composite particles, the ultraviolet-shielding composite particle-containing dispersion liquid, the ultraviolet-shielding composite particle-containing aqueous dispersion element and the ultraviolet-shielding composite particle-containing oil-based dispersion element are blended into an aqueous cosmetic material, such as skin toner or sun-screening gel, the formulation of which was difficult in the related art, the elution of the metal oxide is suppressed, and an aqueous cosmetic material, which is excellent in terms of ultraviolet-shielding function, transparency and a feeling of using the product, can be obtained.

When the cosmetic material is used as a component of a cosmetic product, it is possible to provide a variety of cosmetic products, such as skin care cosmetic products, makeup cosmetic products and body care cosmetic products, which are excellent in terms of ultraviolet-shielding function, transparency and a feeling of using the product. The cosmetic material is particularly preferable for whitening by skin care cosmetic products, base-making by makeup cosmetic products and sun-screening by body care cosmetic products, for which an ultraviolet-shielding function is required.

As described above, according to the ultraviolet-shielding composite particles of the embodiment, when the organic ultraviolet absorbent and the metal oxide particles having an ultraviolet-shielding function are fixed in the resin, it is possible to prevent the alteration and discoloration of the cosmetic material and the impairment in a feeling of using the product, which are caused by the recrystallization of the organic ultraviolet absorbent due to the influence of metal ions.

In addition, since the burden for skin contacted with the organic ultraviolet absorbent is reduced, the particles are highly safe with respect to the human body, and thus it is possible for the cosmetic material to have a stable quality.

In addition, for the ultraviolet-shielding composite particles of the embodiment, since it is not necessary to dissolve the organic ultraviolet absorbent in a specific solvent, it is possible to blend the particles not only into a water-in-oil (W/O) cosmetic material but also into an aqueous cosmetic material, such as an oil-in-water (O/W) cosmetic material, skin toner or sun-screening gel, the formulation of which was difficult in the related art. Therefore, it is possible to increase the degree of freedom for the formulation of the cosmetic material.

In addition, since the average particle diameter of the composite particles is set to 0.05 µm or more and 5 µm or less, even when the composite particles are used in a cosmetic product, there is no rough feeling, and a feeling of using the product is excellent.

In addition, since the organic ultraviolet absorbent and the metal oxide particles having an average particle diameter of 0.003 µm or more and 0.1 µm or less are composited in the resin, visible light rays are not absorbed, and it is possible to maintain transparency which is emphasized in a cosmetic material.

In addition, in a case where a (meth)acrylic resin is used as the resin, it is possible to maintain superior transparency.

In addition, in a case where composite particles are manufactured by combining zinc oxide and the organic ultraviolet absorbent that can shield long-wavelength ultraviolet rays (UVA), it is possible to shield ultraviolet rays (UV) from a longer wavelength compared with a case where the organic ultraviolet absorbent is solely mixed in.

Furthermore, when the cosmetic material of the embodiment is used as a component of a cosmetic product, it is possible to provide a variety of cosmetic products, such as skin care cosmetic products, makeup cosmetic products and body care cosmetic products, which are excellent in terms of ultraviolet-shielding function, transparency and a feeling of using the product. Particularly, in a case where the cosmetic material is used for whitening by skin care cosmetic products, base-making by makeup cosmetic products and sun-screening by body care cosmetic products, for which an ultraviolet-shielding function is required, it is possible to provide a cosmetic product which is excellent in terms of ultraviolet-shielding function, transparency and a feeling of using the product.

Meanwhile, the ultraviolet-shielding composite particles of the embodiment, a dispersion liquid, an aqueous dispersion element and an oil-based dispersion element, all of which include the composite particles, can also be used for a weather-resistant paint which needs to have an ultraviolet-shielding function.

In addition, in a case where the ultraviolet-shielding composite particles, the dispersion liquid, the aqueous dispersion element and the oil-based dispersion element are used in fields other than cosmetic products, there are many cases in which a rough feeling, a feeling of using the product and the like, all of which are emphasized for cosmetic products, do not become serious problems, the dispersant or the resin can be selected more flexibly, and it is possible to increase the degree of freedom for the design and blending of paints and the like.

EXAMPLES

Hereinafter, the invention will be specifically described using examples and comparative examples, but the invention is not limited by the examples.

A. A Moisture Gel for which Zinc Oxide Ultraviolet-Shielding Composite Particles are Used Example 1

(1) Production and Evaluation of a Zinc Oxide-Containing Resin Monomer-Dissolved Liquid "Production of a Resin Monomer Dispersion Liquid"

Fine zinc oxide particles (average particle diameter: 0.02 µm, 200 parts by mass), methyl methacrylate (MMA: resin monomer, 188 parts by mass) and a phosphate surfactant (dispersant, 12 parts by mass) were mixed, and a dispersion treatment was performed for 2 hours using a sand mill, thereby producing a resin monomer dispersion liquid, in which the fine zinc oxide particles were dispersed in the methyl methacrylate (MMA).

"Production of a Resin Monomer-Dissolved Liquid"

Next, a dibenzoyl methane-based compound (avobenzone, PARSOL (registered trademark) 1789, 0.5 parts by mass) (5% by mass) was added to the resin monomer dispersion liquid (9.5 parts by mass), and fully dissolved, thereby producing a zinc oxide-containing resin monomer-dissolved liquid.

The zinc oxide-containing resin monomer-dissolved liquid was coated on a silica plate in an amount of 2 mg/cm$^2$, and the spectral transmittance and SPF value were measured using a Sun Protection Factor (SPF) analyzer UV-1000S (manufactured by Labsphere, INC. USA). The spectral transmittance is illustrated in FIG. 1. In addition, the SPF value of the zinc oxide-containing resin monomer-dissolved liquid was 54.6.

(2) Production and Evaluation of Ultraviolet-Shielding Composite Particles

"Production of an Emulsion"

The above zinc oxide-containing resin monomer-dissolved liquid (100 parts by mass), pure water (234.5 parts by mass), sodium dodecyl benzene sulfonate (0.5 parts by mass), ethylene glycol dimethacrylate (14.0 parts by mass) and a silicone-based defoamer (1.0 part by mass) were mixed, and stirred using a homogenizer AM-7 (manufactured by NISSEI Corporation) at 8000 rpm for 10 minutes, thereby producing an emulsion.

"Production of Ultraviolet-Shielding Composite Particles"

The above emulsion (320.0 parts by mass), pure water (79.856 parts by mass) and potassium persulfate (0.144 parts by mass) were mixed, moved into a reaction apparatus having a stirrer and a thermometer, and subjected to a nitrogen substitution for 1 hour.

Next, the nitrogen-substituted reaction solution was heated to 65° C., and held at 65° C. for 3 hours, and a polymerization reaction was caused. After that, the solution was cooled using ice to stop the polymerization reaction, the obtained polymer was washed using 2-propanol and pure water, then, dried at 90° C., and, after that, ground using a hammer mill, thereby producing ultraviolet-shielding composite particles (ZnO/5% avobenzone/PMMA) of Example 1, which contained 5% by mass of avobenzone.

"Evaluation of the Ultraviolet-Shielding Composite Particles"

The dispersed particle diameter of the above ultraviolet-shielding composite particles (ZnO/5% avobenzone/PMMA) was measured using a dynamic light scattering nanoparticle size analyzer LB-550 (manufactured by Horiba, Ltd.). Here, the ultraviolet-shielding composite particles (ZnO/5% avobenzone/PMMA, 5 parts by mass) were injected into a solution, in which polyether-modified silicone (dispersant, 10 parts by mass) and decamethyl cyclopentasiloxane (cyclic silicone, 85 parts by mass) had been mixed, and dispersed using a disperser to produce an ultraviolet-shielding composite particle (ZnO/5% avobenzone/PMMA)-containing dispersion liquid, the dispersed particle diameter of the dispersion liquid was measured, and the volume particle size distribution and cumulative volume particle size distribution of the dispersion liquid were computed.

As a result, the particle diameter at 10 volume % (D10) in the cumulative volume particle size distribution was 360.5 nm, the particle diameter at 50 volume % (D50) was 505.2 nm, and the particle diameter at 90 volume % (D90) was 664.6 nm.

Figure 2:
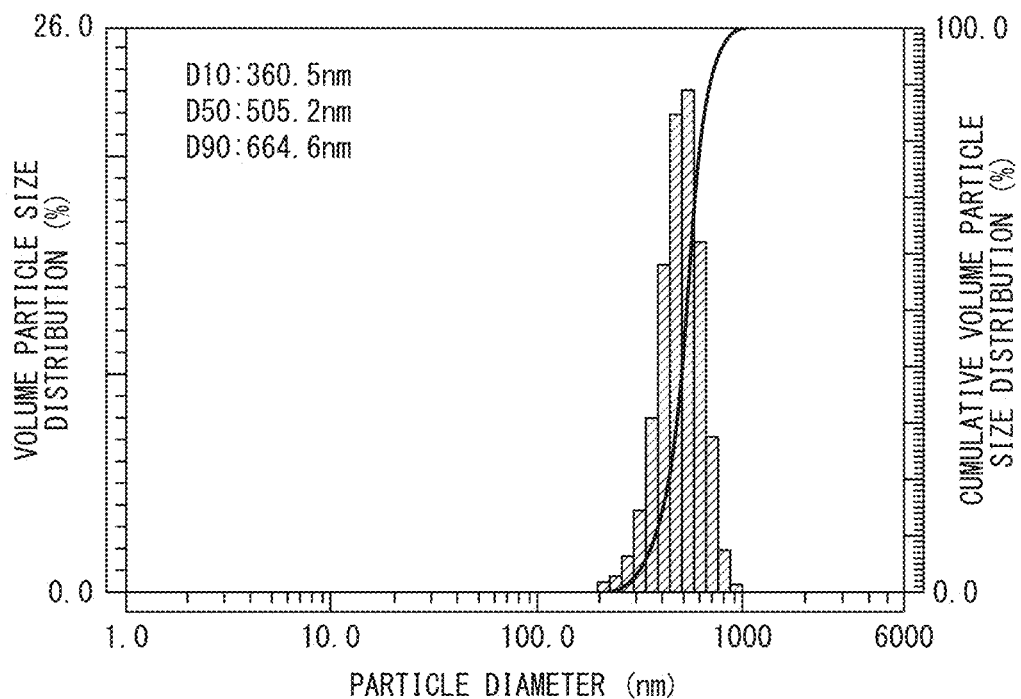
FIG. 2 is a view illustrating the volume particle size distribution and cumulative volume particle size distribution of an ultraviolet-shielding composite particle (ZnO/5% avobenzone/PMMA)-containing dispersion liquid of Example 1 of the invention.
Figure 3:
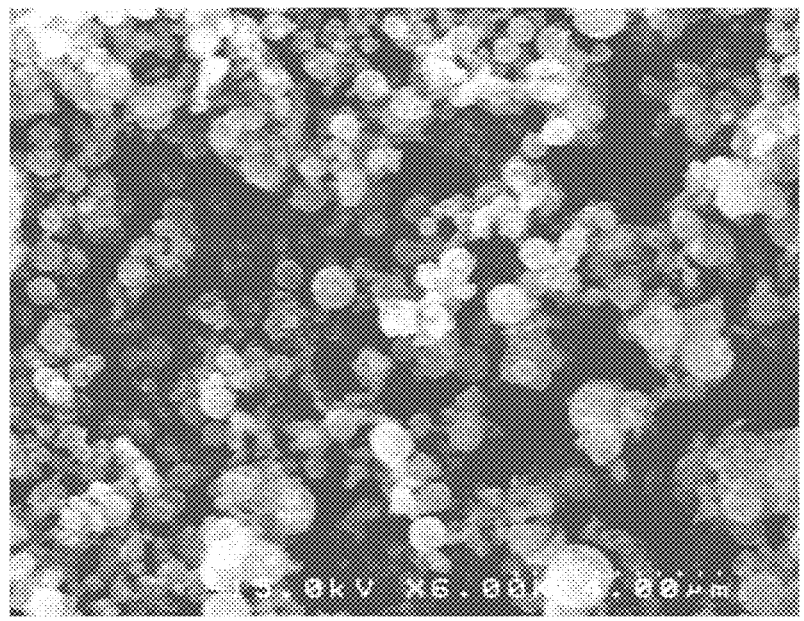
FIG. 3 is a scanning electron microscopic (SEM) image of ultraviolet-shielding composite particles (ZnO/5% avobenzone/PMMA) of Example 1 of the invention.
Figure 4:
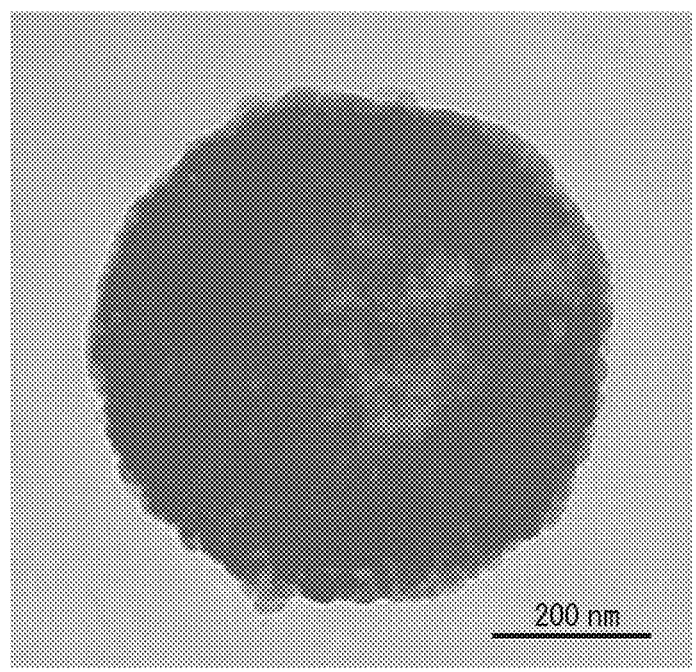
FIG. 4 is a transmission electron microscopic (TEM) image of ultraviolet-shielding composite particles (ZnO/5% avobenzone/PMMA) of Example 1 of the invention.

The volume particle size distribution and cumulative volume particle size distribution of the ultraviolet-shielding composite particle (ZnO/5% avobenzone/PMMA)-containing dispersion liquid are illustrated in FIG. 2. In addition, a scanning electron microscopic (SEM) image of the above ultraviolet-shielding composite particles (ZnO/5% avobenzone/PMMA) is illustrated in FIG. 3, and a transmission electron microscopic (TEM) image of the ultraviolet-shielding composite particles (ZnO/5% avobenzone/PMMA) is illustrated in FIG. 4.

From the TEM image, it was observed that, in the composite particles, the metal oxide particles were encapsulated in the resin particles, and were not exposed on the surfaces. In addition, metal oxide particles exposed on the surfaces of the resin particles were not observed.

The quantity of the residual monomers (methyl methacrylate monomer: MMA) of the ultraviolet-shielding composite particles (ZnO/5% avobenzone/PMMA) was determined using a mass spectrometer GCMS-QP2010 Plus (manufactured by Shimadzu Corporation). Here, the ultraviolet-shielding composite particles (0.5 parts by mass) were sealed in a 22 mL head space vial, the residual monomers obtained by heating and eliminating a gaseous phase portion heated at 150° C. for 40 minutes in the mass spectrometer was measured, and the quantity of the residual monomers was determined using a multiple head space (MHE) method which is a multiple-stage heating and extraction method.

As a result, the quantity of the methyl methacrylate monomer remaining in the ultraviolet-shielding composite particles was 4.8 ppm.

(3) Production of the Ultraviolet-Shielding Composite Particle-Containing Aqueous Dispersion Element The above ultraviolet-shielding composite particles (ZnO/5% avobenzone/PMMA, 20 parts by mass (40% by mass)), ethanol (7.5 parts by mass (15% by mass)) and pure water (22.5 parts by mass (45% by mass)) were mixed to produce the ultraviolet-shielding composite particle (ZnO/5% avobenzone/PMMA)-containing aqueous dispersion element of Example 1, which included 40% by mass of the ultraviolet-shielding composite particles (ZnO/5% avobenzone/PMMA).

(4) Production and Evaluation of a Moisture Gel Using the Ultraviolet-Shielding Composite Particles Sodium carboxy methyl cellulose (1.5 parts by mass (3% by mass)), ethanol (6.25 parts by mass (12.5% by mass)) and glycerin (2.5 parts by mass (5% by mass)) were mixed to produce a solution mixture. Next, the above ultraviolet-shielding composite particle (ZnO/5% avobenzone/PMMA)-containing aqueous dispersion element (25.0 parts by mass (50% by mass)) and pure water (14.75 parts by mass (29.5% by mass)) were mixed with the solution mixture, and stirred at 70° C. for 10 minutes under a condition of heating, thereby producing the moisture gel of Example 1, which contained 20% by mass of the ultraviolet-shielding composite particles (ZnO/5% avobenzone/PMMA).

Figure 5:
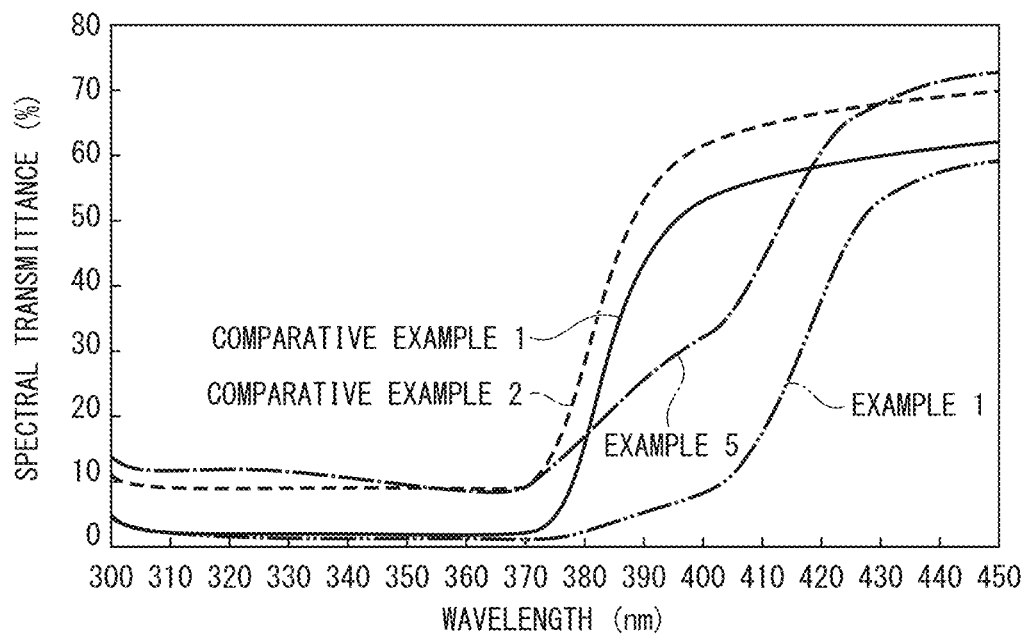
FIG. 5 is a view illustrating the spectral transmittances of respective moisture gels of Examples 1 and 5 and Comparative Examples 1 and 2 of the invention.
Figure 8:
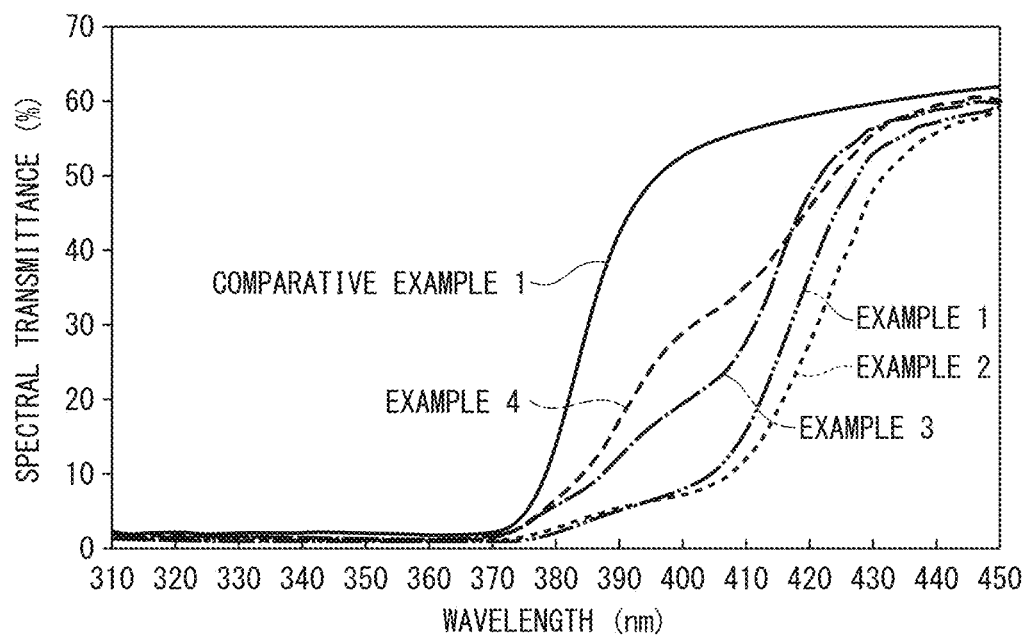
FIG. 8 is a view illustrating the spectral transmittances of respective moisture gels of Examples 1 to 4 and Comparative Example 1 of the invention.

The spectral transmittance of the obtained moisture gel was measured in the same manner as for the above zinc oxide-containing resin monomer-dissolved liquid. The spectral transmittance of the moisture gel is illustrated in FIGS. 5 and 8.

In addition, the SPF value of the moisture gel was measured to be 46.1.

In addition, the viscosity of the moisture gel was measured using a B-type viscometer (manufactured by Toki Sangyo Co., Ltd.), and was 5,000 mPa·s.

Furthermore, after the moisture gel was left to stand at 25° C. for 120 hours, a significant decrease in the viscosity due to the joint use of metal ions and carbomer was not observed, and the recrystallization of the avobenzone, the separation of the moisture gel and the like, which were caused by the joint use of the metal ions and the organic ultraviolet absorbent, were not observed. This indicates that zinc oxide and avobenzone are fixed in the ultraviolet-shielding composite particles in a stable state.

Next, when the moisture gel was spread on skin, the moisture gel was transparent.

Example 2

A zinc oxide-containing resin monomer-dissolved liquid of Example 2 was produced in the same manner as in Example 1 except that a dibenzoyl methane-based compound (avobenzone, PARSOL (registered trademark) 1789, 1 part by mass) (10% by mass) was added to the resin monomer dispersion liquid (9 parts by mass).

The spectral transmittance and SPF value of the zinc oxide-containing resin monomer-dissolved liquid were measured in the same manner as in Example 1. The spectral transmittance of the zinc oxide-containing resin monomer-dissolved liquid is illustrated in FIG. 1.

In addition, the SPF value of the zinc oxide-containing resin monomer-dissolved liquid was 56.3.

Ultraviolet-shielding composite particles (ZnO/10% avobenzone/PMMA) of Example 2, which contained 10% by mass of the dibenzoyl methane-based compound (avobenzone, PARSOL (registered trademark) 1789), were produced in the same manner as in Example 1 using the above resin monomer-dissolved liquid.

An aqueous dispersion element including 40% by mass of the ultraviolet-shielding composite particles (ZnO/10% avobenzone/PMMA) was produced in the same manner as in Example 1 using the above ultraviolet-shielding composite particles (ZnO/10% avobenzone/PMMA).

Next, a moisture gel of Example 2, which contained 20% by mass of the above ultraviolet-shielding composite particles (ZnO/10% avobenzone/PMMA), was produced in the same manner as in Example 1 using an aqueous dispersion element including 40% by mass of the above ultraviolet-shielding composite particles (ZnO/10% avobenzone/PMMA).

The spectral transmittance of the obtained moisture gel is illustrated in FIG. 8.

Example 3

A zinc oxide-containing resin monomer-dissolved liquid of Example 3 was produced in the same manner as in Example 1 except that a dibenzoyl methane-based compound (avobenzone, PARSOL (registered trademark) 1789, 0.1 part by mass) (1% by mass) was added to the resin monomer dispersion liquid (9.9 parts by mass).

The spectral transmittance and SPF value of the zinc oxide-containing resin monomer-dissolved liquid were measured in the same manner as in Example 1. The spectral transmittance of the zinc oxide-containing resin monomer-dissolved liquid is illustrated in FIG. 1.

In addition, the SPF value of the zinc oxide-containing resin monomer-dissolved liquid was 49.9.

Ultraviolet-shielding composite particles (ZnO/1% avobenzone/PMMA) of Example 3, which contained 1% by mass of avobenzone, were produced in the same manner as in Example 1 using the above resin monomer-dissolved liquid.

An aqueous dispersion element including 40% by mass of the ultraviolet-shielding composite particles (ZnO/1% avobenzone/PMMA) was produced in the same manner as in Example 1 using the above ultraviolet-shielding composite particles (ZnO/1% avobenzone/PMMA).

Next, a moisture gel of Example 3, which contained 20% by mass of the ultraviolet-shielding composite particles (ZnO/1% avobenzone/PMMA), was produced in the same manner as in Example 1 using an aqueous dispersion element including 40% by mass of the above ultraviolet-shielding composite particles (ZnO/1% avobenzone/PMMA).

The spectral transmittance of the obtained moisture gel is illustrated in FIG. 8.

Example 4

A zinc oxide-containing resin monomer-dissolved liquid of Example 4 was produced in the same manner as in Example 1 except that a dibenzoyl methane-based compound (avobenzone, PARSOL (registered trademark) 1789, 0.05 part by mass) (0.5% by mass) was added to the resin monomer dispersion liquid (9.95 parts by mass).

The spectral transmittance and SPF value of the zinc oxide-containing resin monomer-dissolved liquid were measured in the same manner as in Example 1. The spectral transmittance of the zinc oxide-containing resin monomer-dissolved liquid is illustrated in FIG. 1.

In addition, the SPF value of the zinc oxide-containing resin monomer-dissolved liquid was 44.1.

Ultraviolet-shielding composite particles (ZnO/0.5% avobenzone/PMMA) of Example 4, which contained 0.5% by mass of avobenzone, were produced in the same manner as in Example 1 using the above zinc oxide-containing resin monomer-dissolved liquid.

An aqueous dispersion element including 40% by mass of the ultraviolet-shielding composite particles (ZnO/0.5% avobenzone/PMMA) was produced in the same manner as in Example 1 using the above ultraviolet-shielding composite particles (ZnO/0.5% avobenzone/PMMA).

Next, a moisture gel of Example 4, which contained 20% by mass of the ultraviolet-shielding composite particles (ZnO/0.5% avobenzone/PMMA), was produced in the same manner as in Example 1 using an aqueous dispersion element including 40% by mass of the above ultraviolet-shielding composite particles (ZnO/0.5% avobenzone/PMMA).

The spectral transmittance of the obtained moisture gel is illustrated in FIG. 8.

Example 5

A moisture gel of Example 5, which contained 10% by mass of the ultraviolet-shielding composite particles (ZnO/5% avobenzone/PMMA), was produced in the same manner as in Example 1 except that the ultraviolet-shielding composite particle (ZnO/5% avobenzone/PMMA)-containing aqueous dispersion element obtained in Example 1 was set to 12.5 parts by mass (25% by mass), and pure water was set to 27.25 parts by mass (54.5% by mass).

The spectral transmittance of the obtained moisture gel was measured in the same manner as in Example 1. The spectral transmittance of the moisture gel is illustrated in FIG. 5.

In addition, the SPF value of the moisture gel was measured in the same manner as in Example 1 and was 8.6.

In addition, the viscosity of the moisture gel was measured in the same manner as in Example 1, and was 1,200 mPa·s.

Furthermore, after the moisture gel was left to stand at 25° C. for 120 hours, a significant decrease in the viscosity, the recrystallization of the avobenzone, the separation of the moisture gel and the like were not observed. In addition, when the moisture gel was spread on skin, the moisture gel was transparent.

Comparative Example 1

Fine zinc oxide particles (average particle diameter: 0.02 µm, 200 parts by mass), methyl methacrylate (MMA: resin monomer, 188 parts by mass) and a phosphate surfactant (dispersant, 12 parts by mass) were mixed, and a dispersion treatment was performed for 2 hours using a sand mill, thereby producing a resin monomer dispersion liquid, in which the fine zinc oxide particles were dispersed in the methyl methacrylate (MMA).

The spectral transmittance and SPF value of the obtained resin monomer dispersion liquid were measured in the same manner as in Example 1. The spectral transmittance of the resin monomer dispersion liquid is illustrated in FIG. 1.

In addition, the SPF value of the resin monomer dispersion liquid was 41.7.

Next, ultraviolet-shielding composite particles (ZnO/PMMA) of Comparative Example 1 were produced in the same manner as in Example 1 using the above resin monomer dispersion liquid.

The quantity of the monomers (methyl methacrylate monomer: MMA) remaining in the obtained ultraviolet-shielding composite particles (ZnO/PMMA) was determined in the same manner as in Example 1. As a result, the quantity of the methyl methacrylate monomer remaining in the ultraviolet-shielding composite particles (ZnO/PMMA) was 10.2 ppm.

The ultraviolet-shielding composite particle (ZnO/PMMA)-containing aqueous dispersion element of Comparative Example 1, which contained 40% by mass of the ultraviolet-shielding composite particles (ZnO/PMMA), was produced in the same manner as in Example 1 using the above ultraviolet-shielding composite particles (ZnO/PMMA).

Next, a moisture gel of Comparative Example 1, which contained 20% by mass of the ultraviolet-shielding composite particles (ZnO/PMMA), was produced in the same manner as in Example 1 using the ultraviolet-shielding composite particle (ZnO/PMMA)-containing dispersion element.

The spectral transmittance of the obtained moisture gel was measured in the same manner as in Example 1. The spectral transmittance of the moisture gel is illustrated in FIGS. 5 and 8.

In addition, the SPF value of the moisture gel was measured in the same manner as in Example 1 and was 33.1.

In addition, the viscosity of the moisture gel was measured in the same manner as in Example 1, and was 12,400 mPa·s.

Comparative Example 2

A moisture gel of Comparative Example 2, which contained 10% by mass of the ultraviolet-shielding composite particles (ZnO/PMMA), was produced in the same manner as in Example 1 using the ultraviolet-shielding composite particle (ZnO/PMMA)-containing dispersion element of Comparative Example 1 except that the ultraviolet-shielding composite particle (ZnO/PMMA)-containing aqueous dispersion element was set to 12.5 parts by mass (25% by mass), and pure water was set to 27.25 parts by mass (54.5% by mass).

The spectral transmittance of the obtained moisture gel was measured in the same manner as in Example 1. The spectral transmittance of the moisture gel is illustrated in FIG. 5.

In addition, the SPF value of the moisture gel was measured in the same manner as in Example 1 and was 10.3.

In addition, the viscosity of the moisture gel was measured in the same manner as in Example 1, and was 4,800 mPa·s.

When the spectral transmittances of Examples 1 and 5 were compared with the spectral transmittances of Comparative Examples 1 and 2, it was found that it was possible to shield ultraviolet rays in a longer-wavelength region by making zinc oxide and avobenzone into composite particles.

In addition, when the spectral transmittances of Examples 1 and 5 were compared with the spectral transmittances of Comparative Examples 2 to 4, it was found that it was possible to shield ultraviolet rays in a longer-wavelength region by making zinc oxide and avobenzone into composite particles compared to a state in which zinc oxide and avobenzone were simply mixed.

B. Titanium Oxide Ultraviolet-Shielding Composite particles

Example 6

"Production of a Titanium Oxide-Containing Resin Monomer-Dissolved Liquid"

Methyl methacrylate (MMA: resin monomer, 239.7 parts by mass) and a dibenzoyl methane-based compound (avobenzone, PARSOL (registered trademark) 1789, 20.3 parts by mass) (7.8% by mass) were added, and fully dissolved, thereby producing a resin monomer-dissolved liquid including 7.8% by mass of avobenzone.

"Production of a Resin Monomer Dispersion Liquid"

Next, fine titanium oxide particles (average particle diameter: 0.02 μm, 120 parts by mass), the resin monomer-dissolved liquid including 7.8% by mass of avobenzone (256 parts by mass) and a phosphate surfactant (dispersant, 24 parts by mass) were mixed, and a dispersion treatment was performed for 3 hours using a sand mill, thereby producing a resin monomer dispersion liquid, in which the fine titanium oxide particles were dispersed in the resin monomer-dissolved liquid including 5% by mass of avobenzone.

"Production of an Emulsion"

The above resin monomer dispersion liquid (100 parts by mass), pure water (234.5 parts by mass), sodium dodecyl benzene sulfonate (0.5 parts by mass), ethylene glycol dimethacrylate (14.0 parts by mass) and a silicone-based defoamer (1.0 part by mass) were mixed, and stirred using a homogenizer AM-7 (manufactured by NISSEI Corporation) at 8000 rpm. for 10 minutes, thereby producing an emulsion.

"Production of Ultraviolet-Shielding Composite Particles"

The above emulsion (320.0 parts by mass), pure water (79.856 parts by mass) and potassium persulfate (0.144 parts by mass) were mixed, moved into a reaction apparatus having a stirrer and a thermometer, and subjected to a nitrogen substitution for 1 hour.

Next, the nitrogen-substituted reaction solution was heated to 65° C., held at 65° C. for 3 hours, and a polymerization reaction was caused. After that, the solution was cooled using ice to stop the polymerization reaction, the obtained polymer was washed using 2-propanol and pure water, and then, dried at 90° C., thereby producing ultraviolet-shielding composite particles (TiO$_2$/5% avobenzone/PMMA) of Example 6.

Figure 6:
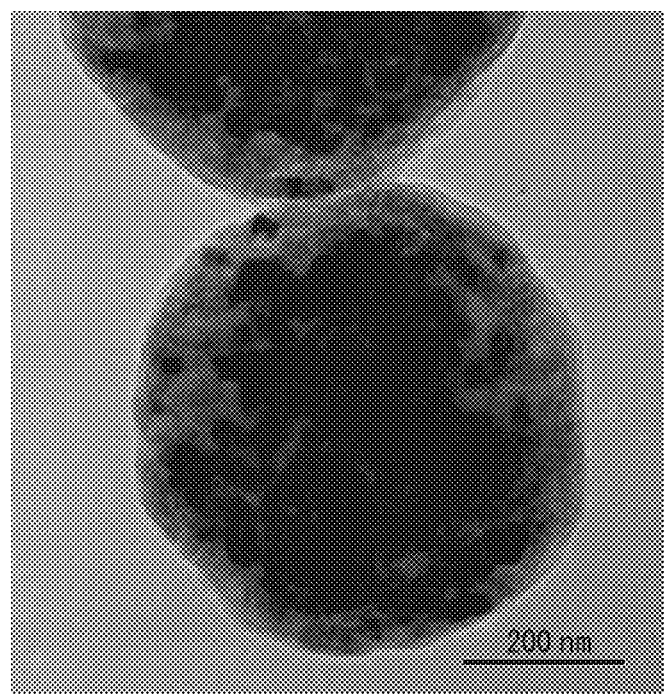
FIG. 6 is a transmission electron microscopic (TEM) image of ultraviolet-shielding composite particles (TiO$_2$/5% avobenzone/PMMA) of Example 6 of the invention.

A transmission electron microscopic (TEM) image of the ultraviolet-shielding composite particles (TiO$_2$/5% avobenzone/PMMA) is illustrated in FIG. 6. It was observed that, in the composite particles, the metal oxide particles were encapsulated in the resin particles, and were not exposed on the surfaces. In addition, metal oxide particles exposed on the surfaces of the resin particles were not observed.

Comparative Example 3

Fine titanium oxide particles (average particle diameter: 0.02 μm, 120 parts by mass), methyl methacrylate (MMA, 256 parts by mass) and a phosphate surfactant (dispersant, 24 parts by mass) were mixed, and a dispersion treatment was performed for 3 hours using a sand mill, thereby producing a resin monomer dispersion liquid, in which the fine titanium oxide particles were dispersed in the methyl methacrylate (MMA).

"Production of an Emulsion"

The above resin monomer dispersion liquid (100 parts by mass), pure water (234.5 parts by mass), sodium dodecyl benzene sulfonate (0.5 parts by mass), ethylene glycol dimethacrylate (14.0 parts by mass) and a silicone-based defoamer (1.0 part by mass) were mixed, and stirred using a homogenizer AM-7 (manufactured by NISSEI Corporation) at 8000 rpm for 10 minutes, thereby producing an emulsion.

"Production of Ultraviolet-Shielding Composite Particles"

Next, the obtained emulsion (320.0 parts by mass), pure water (79.856 parts by mass) and potassium persulfate (0.144 parts by mass) were mixed, moved into a reaction apparatus having a stirrer and a thermometer, and subjected to a nitrogen substitution for 1 hour.

Next, the nitrogen-substituted reaction solution was heated to 65° C., held at 65° C. for 3 hours, and a polymerization reaction was caused. After that, the solution was cooled using ice to stop the polymerization reaction, the obtained polymer was washed using 2-propanol and pure water, and then, dried at 90° C., thereby producing ultraviolet-shielding composite particles ($TiO_2$/PMMA) of Comparative Example 3.

C. Simple Sunscreen Using the Ultraviolet-Shielding Composite Particles

Example 7

"Production of an Ultraviolet-Shielding Composite Particle-Containing Oil-Based Dispersion Element"

The ultraviolet-shielding composite particles obtained in Example 1 (ZnO/5% avobenzone/PMMA, 36 parts by mass), decamethyl cyclopentasiloxane (D5) SH245 (manufactured by Dow Corning Toray Co., Ltd., 75 parts by mass) and polyether-modified silicone (9 parts by mass) were mixed, and dispersed at 2500 rpm for 3 hours using a sand mill, thereby producing an ultraviolet-shielding composite particle (ZnO/5% avobenzone/PMMA)-containing oil-based dispersion element of Example 7, which included 30% by mass of the ultraviolet-shielding composite particles (ZnO/5% avobenzone/PMMA).

"Production of an Ultraviolet-Shielding Composite Particle-Containing Simple Sunscreen"

The above ultraviolet-shielding composite particle (ZnO/5% avobenzone/PMMA)-containing oil-based dispersion element (66.8 parts by mass), linear polyether-modified silicone (manufactured by Shin-Etsu Chemical Co., Ltd., KF6028, 9.6 parts by mass) as a film-forming agent and branched polyether-modified silicone (manufactured by Shin-Etsu Chemical Co., Ltd., KF6017, 10.4 parts by mass) as an emulsifier were injected into an aqueous solution, in which pure water (8.2 parts by mass) and 1,3-butanediol (5.0 parts by mass) had been mixed in advance, and well mixed using a mortar, thereby producing a simple sunscreen of Example 7, which contained 20% by mass of the ultraviolet-shielding composite particles (ZnO/5% avobenzone/PMMA).

Figure 7:
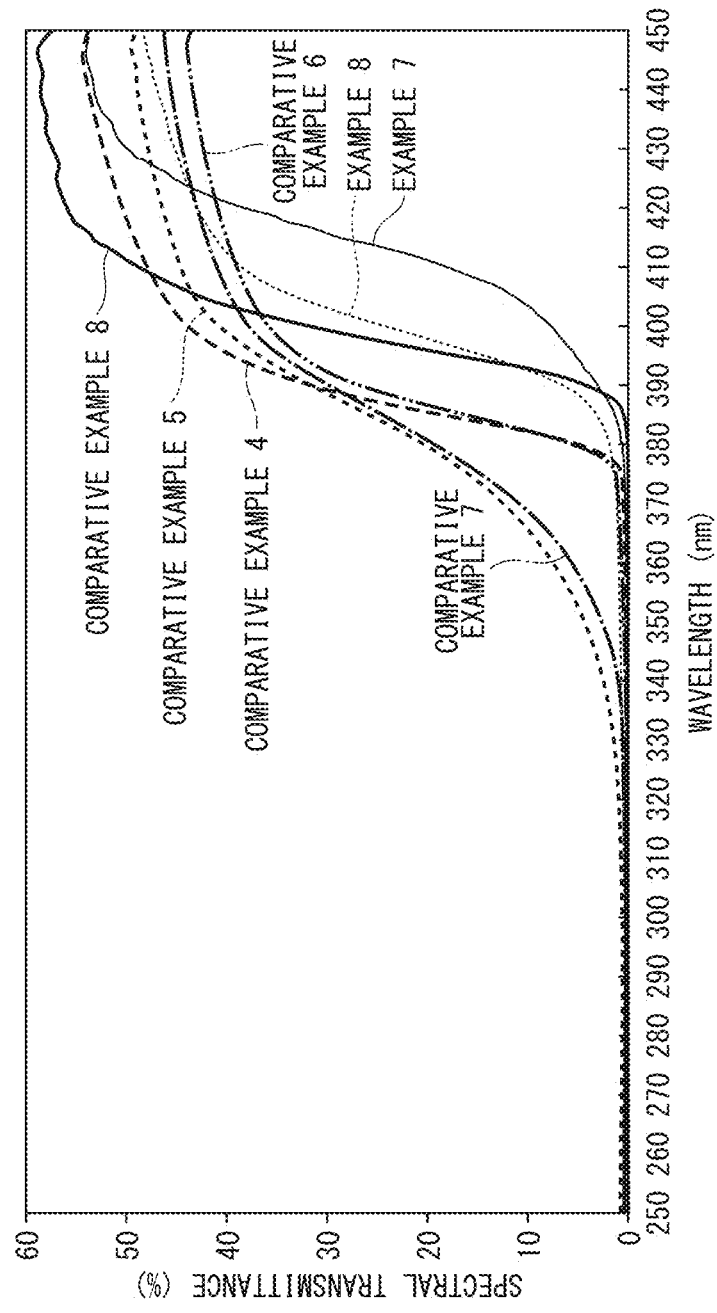
FIG. 7 is a view illustrating the spectral transmittances of respective simple sunscreens of Examples 7 and 8 and Comparative Examples 4 to 8 of the invention.
Figure 13:
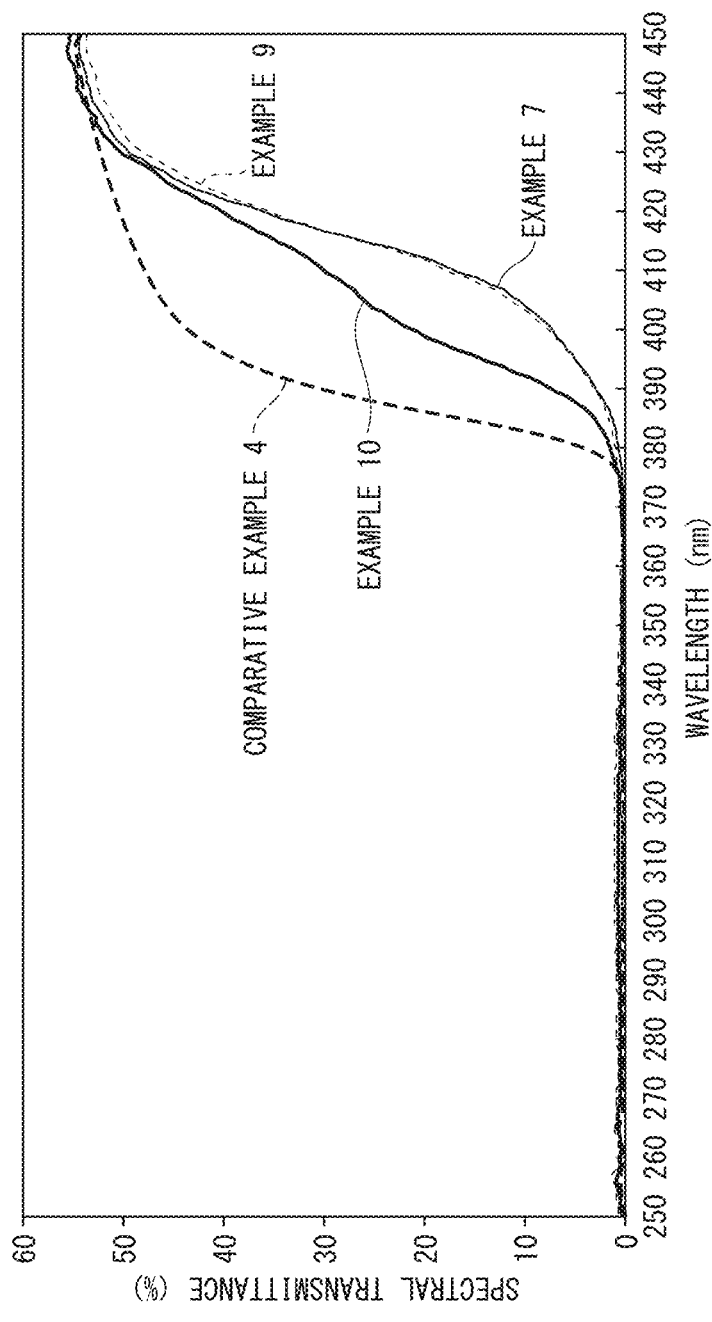
FIG. 13 is a view illustrating the spectral transmittances of respective simple sunscreens of Examples 7, 9 and 10 and Comparative Example 4 of the invention.
Figure 18:
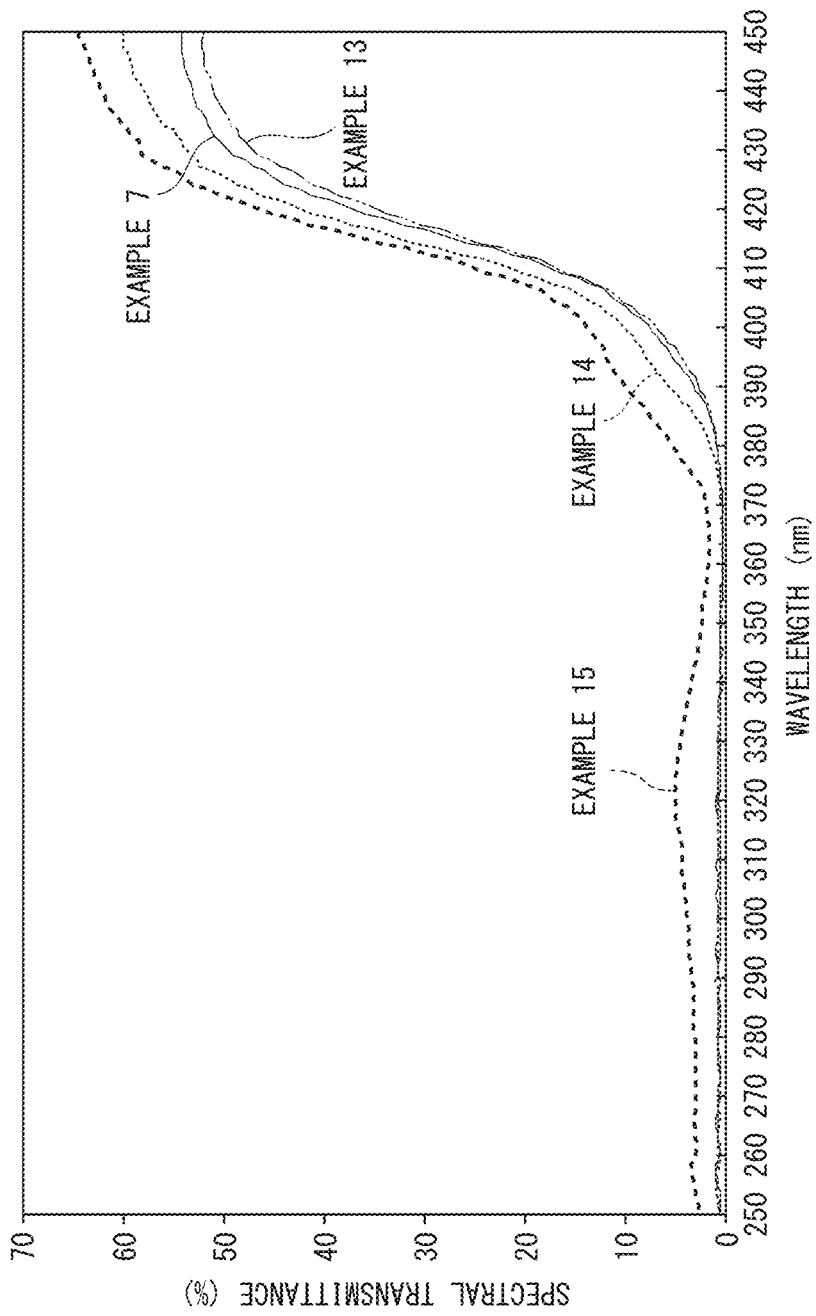
FIG. 18 is a view illustrating the spectral transmittances of respective simple sunscreens of Examples 7 and 13 to 15 of the invention.

The spectral transmittance of the obtained simple sunscreen was measured in the same manner as in Example 1. The spectral transmittance of the simple sunscreen is illustrated in FIGS. 7, 13 and 18.

Example 8

An ultraviolet-shielding composite particle ($TiO_2$/5% avobenzone/PMMA)-containing oil-based dispersion element of Example 8, which included 30% by mass of the ultraviolet-shielding composite particles ($TiO_2$/5% avobenzone/PMMA), was produced in the same manner as in Example 7 except that the ultraviolet-shielding composite particles ($TiO_2$/5% avobenzone/PMMA) obtained in Example 6 were used instead of the ultraviolet-shielding composite particles (ZnO/5% avobenzone/PMMA) obtained in Example 1.

A simple sunscreen of Example 8, which contained 20% by mass of the ultraviolet-shielding composite particles ($TiO_2$/5% avobenzone/PMMA), was produced in the same manner as in Example 7 except that the above ultraviolet-shielding composite particle ($TiO_2$/5% avobenzone/PMMA)-containing oil-based dispersion element was used instead of the above ultraviolet-shielding composite particle (ZnO/5% avobenzone/PMMA)-containing oil-based dispersion element obtained in Example 7.

Figure 14:
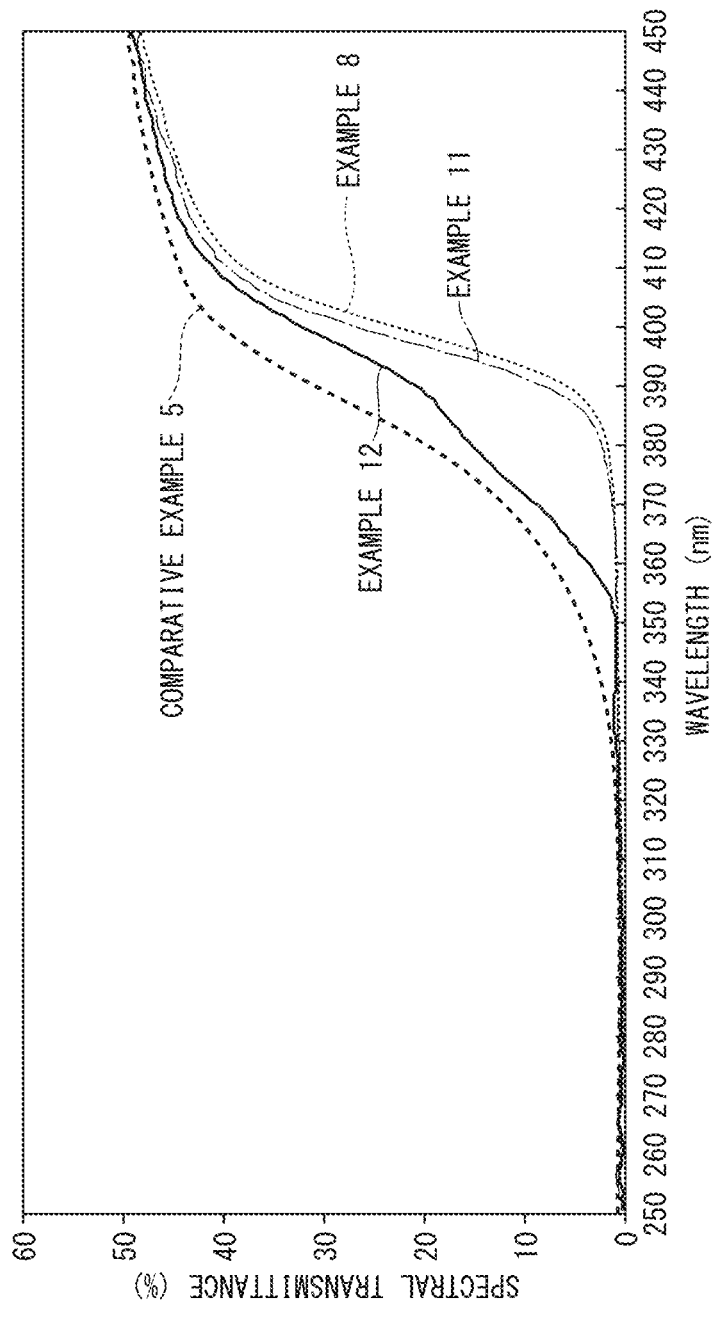
FIG. 14 is a view illustrating the spectral transmittances of respective simple sunscreens of Examples 8, 11 and 12 and Comparative Example 5 of the invention.

The spectral transmittance of the obtained simple sunscreen was measured in the same manner as in Example 1. The spectral transmittance of the simple sunscreen is illustrated in FIGS. 7 and 14.

Comparative Example 4

A fine zinc oxide particle-containing oil-based dispersion element of Comparative Example 4, which included 30% by mass of the fine zinc oxide particles, was produced in the same manner as in Example 7 except that fine zinc oxide particles (ZnO, average particle diameter: 0.02 μm) were used instead of the ultraviolet-shielding composite particles (ZnO/5% avobenzone/PMMA) obtained in Example 1.

A simple sunscreen of Comparative Example 4, which contained 20% by mass of the fine zinc oxide particles, was produced in the same manner as in Example 7 using the above fine zinc oxide particle-containing oil-based dispersion element.

The spectral transmittance of the obtained simple sunscreen was measured in the same manner as in Example 1. The spectral transmittance of the simple sunscreen is illustrated in FIGS. 7 and 13.

Comparative Example 5

A fine titanium oxide particle-containing oil-based dispersion element of Comparative Example 5, which included 30% by mass of the fine titanium oxide particles, was produced in the same manner as in Example 7 except that fine titanium oxide particles ($TiO_2$, average particle diameter: 0.02 μm) were used instead of the ultraviolet-shielding composite particles (ZnO/5% avobenzone/PMMA) obtained in Example 1.

A simple sunscreen of Comparative Example 5, which contained 20% by mass of the fine titanium oxide particles, was produced in the same manner as in Example 7 using the above fine titanium oxide particle-containing oil-based dispersion element.

The spectral transmittance of the obtained simple sunscreen was measured in the same manner as in Example 1. The spectral transmittance of the simple sunscreen is illustrated in FIGS. 7 and 14.

Comparative Example 6

An ultraviolet-shielding composite particle (ZnO/PMMA)-containing oil-based dispersion element of Comparative Example 6, which included 30% by mass of ultraviolet-shielding composite particles (ZnO/PMMA), was produced in the same manner as in Example 7 except that the ultraviolet-shielding composite particles (ZnO/PMMA) of Comparative Example 1 were used instead of the ultraviolet-shielding composite particles (ZnO/5% avobenzone/PMMA) obtained in Example 1.

A simple sunscreen of Comparative Example 6, which contained 20% by mass of the ultraviolet-shielding composite particles (ZnO/PMMA), was produced in the same manner as in Example 7 using the above ultraviolet-shielding composite particle (ZnO/PMMA)-containing oil-based dispersion element.

The spectral transmittance of the obtained simple sunscreen was measured in the same manner as in Example 1. The spectral transmittance of the simple sunscreen is illustrated in FIG. 7.

Comparative Example 7

An ultraviolet-shielding composite particle ($TiO_2$/PMMA)-containing oil-based dispersion element of Comparative Example 7, which included 30% by mass of ultraviolet-shielding composite particles ($TiO_2$/PMMA), was produced in the same manner as in Example 7 except that the ultraviolet-shielding composite particles ($TiO_2$/PMMA) of Comparative Example 3 were used instead of the ultraviolet-shielding composite particles (ZnO/5% avobenzone/PMMA) obtained in Example 1.

A simple sunscreen of Comparative Example 7, which contained 20% by mass of the ultraviolet-shielding composite particles ($TiO_2$/PMMA), was produced in the same manner as in Example 7 using the above ultraviolet-shielding composite particle ($TiO_2$/PMMA)-containing oil-based dispersion element.

The spectral transmittance of the obtained simple sunscreen was measured in the same manner as in Example 1. The spectral transmittance of the simple sunscreen is illustrated in FIG. 7.

Comparative Example 8

A dibenzoyl methane-based compound (avobenzone, PARSOL (registered trademark) 1789, 1.5 parts by mass), decamethyl cyclopentasiloxane (D5) SH245 (manufactured by Dow Corning Toray Co., Ltd., 91 parts by mass) and polyether-modified silicone (7.5 parts by mass) were mixed, and dissolved at 85° C., thereby producing an avobenzone-containing oil-based dispersion element of Comparative Example 8, which included 1.5% by mass of avobenzone.

A simple sunscreen of Comparative Example 8, which contained 1.0% by mass of avobenzone, was produced in the same manner as in Example 7 using the above avobenzone-containing oil-based dispersion element.

The spectral transmittance of the obtained simple sunscreen was measured in the same manner as in Example 1. The spectral transmittance of the simple sunscreen is illustrated in FIG. 7.

D. A Simple Sunscreen Using the Ultraviolet-Shielding Composite Particles Having a Changed Surface-Coating State.

Example 9

"Production of an Emulsion"

The resin monomer-dissolved liquid obtained in Example 1 (100 parts by mass), pure water (234.9 parts by mass), sodium dodecyl benzene sulfonate (0.1 parts by mass), ethylene glycol dimethacrylate (14.0 parts by mass) and a silicone-based defoamer (1.0 part by mass) were mixed, and stirred using a homogenizer, thereby producing an emulsion.

"Production of Ultraviolet-Shielding Composite Particles"

Next, ultraviolet-shielding composite particles (ZnO/5% avobenzone/PMMA) were produced using the above emulsion in the same manner as in Example 1.

Figure 9:
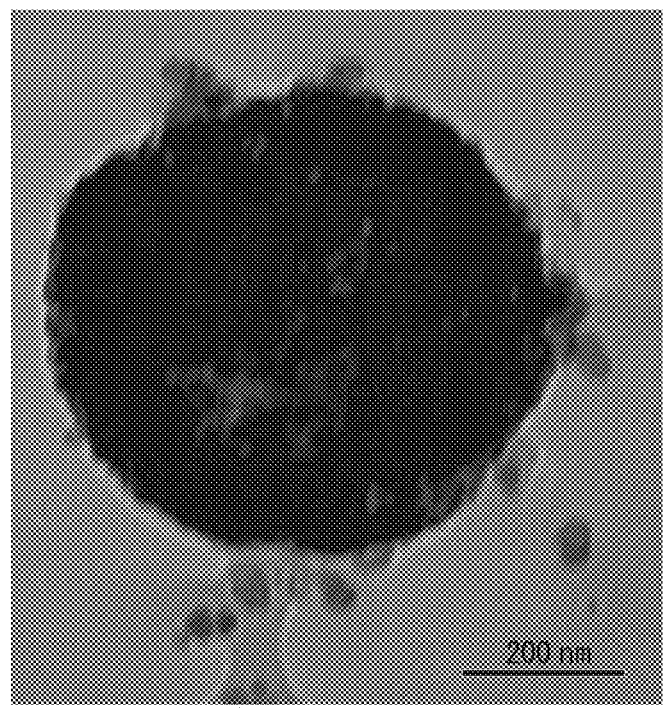
FIG. 9 is a transmission electron microscopic (TEM) image of ultraviolet-shielding composite particles (ZnO/5% avobenzone/PMMA) of Example 9 of the invention.

A transmission electron microscopic (TEM) image of the ultraviolet-shielding composite particles (ZnO/5% avobenzone/PMMA) is illustrated in FIG. 9.

In the ultraviolet-shielding composite particles, not only the resin particles having the fine metal oxide particles encapsulated in the composite particles but also the composite particles having the metal oxide particles exposed on the surfaces of the resin particles or the composite particles having the metal oxide particles partially coated with the resin were observed.

"Production of an Ultraviolet-Shielding Composite Particle-Containing Oil-Based Dispersion Element"

Next, an ultraviolet-shielding composite particle (ZnO/5% avobenzone/PMMA)-containing oil-based dispersion element, which included 30% by mass of the ultraviolet-shielding composite particles (ZnO/5% avobenzone/PMMA), was produced in the same manner as in Example 7 using the above ultraviolet-shielding composite particles (ZnO/5% avobenzone/PMMA).

"Production of an Ultraviolet-Shielding Composite Particle-Containing Simple Sunscreen"

Next, a simple sunscreen of Example 9, which contained 20% by mass of the ultraviolet-shielding composite particles (ZnO/5% avobenzone/PMMA), was produced in the same manner as in Example 7 using the above ultraviolet-shielding composite particles (ZnO/5% avobenzone/PMMA)-containing oil-based dispersion element.

The spectral transmittance of the obtained simple sunscreen was measured in the same manner as in Example 1. The spectral transmittance of the simple sunscreen is illustrated in FIG. 13.

Example 10

The resin monomer-dissolved liquid obtained in Example 1 (100 parts by mass), pure water (234.99 parts by mass), sodium dodecyl benzene sulfonate (0.01 parts by mass), ethylene glycol dimethacrylate (14.0 parts by mass) and a silicone-based defoamer (1.0 part by mass) were mixed, and stirred using a homogenizer, thereby producing an emulsion.

Next, ultraviolet-shielding composite particles (ZnO/5% avobenzone/PMMA) were produced using the emulsion obtained above in the same manner as in Example 1.

Figure 10:
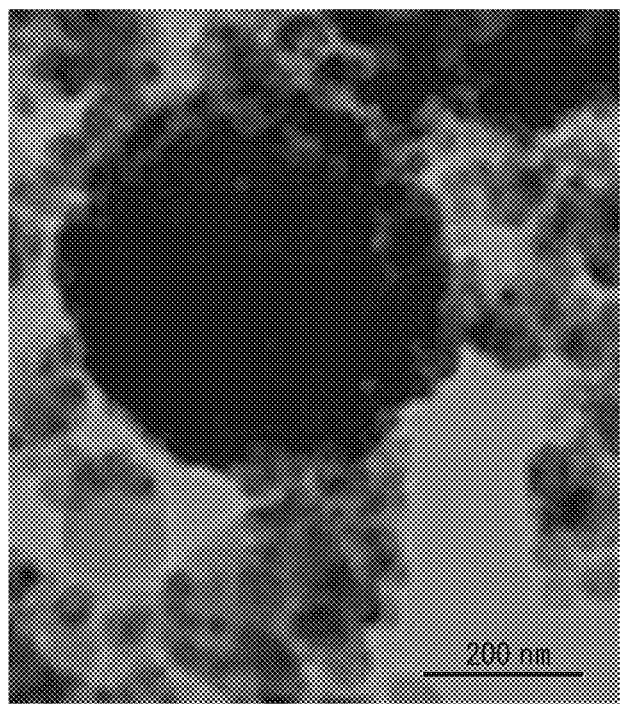
FIG. 10 is a transmission electron microscopic (TEM) image of ultraviolet-shielding composite particles (ZnO/5% avobenzone/PMMA) of Example 10 of the invention.

A transmission electron microscopic (TEM) image of the ultraviolet-shielding composite particles (ZnO/5% avobenzone/PMMA) is illustrated in FIG. 10.

In the ultraviolet-shielding composite particles, not only the resin particles having the fine metal oxide particles encapsulated in the composite particles but also the composite particles having the metal oxide particles exposed on the surfaces of the resin particles, the composite particles having the metal oxide particles partially coated with the resin or particles considered as the metal oxide particles itself, which is not coated with the resin, were observed.

Next, an ultraviolet-shielding composite particle (ZnO/5% avobenzone/PMMA)-containing oil-based dispersion element, which included 30% by mass of the ultraviolet-shielding composite particles (ZnO/5% avobenzone/PMMA), was produced in the same manner as in Example 7 using the above ultraviolet-shielding composite particles (ZnO/5% avobenzone/PMMA).

Next, a simple sunscreen of Example 10, which contained 20% by mass of the ultraviolet-shielding composite particles (ZnO/5% avobenzone/PMMA), was produced in the same manner as in Example 7 using the above ultraviolet-shielding composite particle (ZnO/5% avobenzone/PMMA)-containing oil-based dispersion element.

The spectral transmittance of the obtained simple sunscreen was measured in the same manner as in Example 1. The spectral transmittance of the simple sunscreen is illustrated in FIG. 13.

Example 11

A resin monomer dispersion liquid obtained by dispersing the fine titanium oxide particles obtained in Example 6 in a resin monomer-dissolved liquid of 5% by mass avobenzone (100 parts by mass), pure water (234.9 parts by mass), sodium dodecyl benzene sulfonate (0.1 parts by mass), ethylene glycol dimethacrylate (14.0 parts by mass) and a silicone-based defoamer (1.0 part by mass) was mixed, and stirred using a homogenizer, thereby producing an emulsion.

Next, ultraviolet-shielding composite particles ($TiO_2$/5% avobenzone/PMMA) were produced in the same manner as in Example 6 using the above emulsion.

Figure 11:
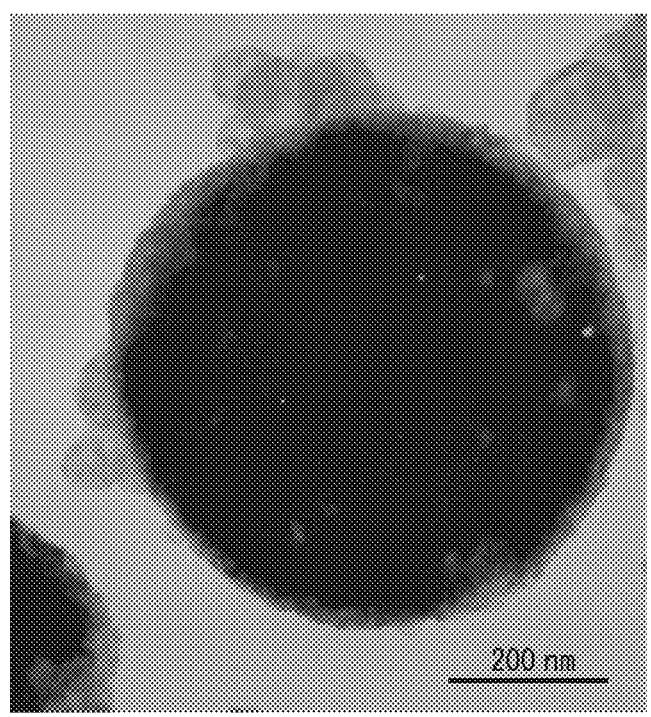
FIG. 11 is a transmission electron microscopic (TEM) image of ultraviolet-shielding composite particles (TiO$_2$/5% avobenzone/PMMA) of Example 11 of the invention.

A transmission electron microscopic (TEM) image of the obtained ultraviolet-shielding composite particles ($TiO_2$/5% avobenzone/PMMA) is illustrated in FIG. 11.

In the ultraviolet-shielding composite particles, not only the resin particles having the fine metal oxide particles encapsulated in the composite particles but also the composite particles having the metal oxide particles exposed on the surfaces of the resin particles or the composite particles having the metal oxide particles partially coated with the resin were observed.

An ultraviolet-shielding composite particle ($TiO_2$/5% avobenzone/PMMA)-containing oil-based dispersion element, which included 30% by mass of the ultraviolet-shielding composite particles ($TiO_2$/5% avobenzone/PMMA), was produced in the same manner as in Example 7 using the above ultraviolet-shielding composite particles ($TiO_2$/5% avobenzone/PMMA).

Next, a simple sunscreen of Example 11, which contained 20% by mass of the ultraviolet-shielding composite particles ($TiO_2$/5% avobenzone/PMMA), was produced in the same manner as in Example 7 using the above ultraviolet-shielding composite particle ($TiO_2$/5% avobenzone/PMMA)-containing oil-based dispersion element.

The spectral transmittance of the obtained simple sunscreen was measured in the same manner as in Example 1. The spectral transmittance of the simple sunscreen is illustrated in FIG. 14.

Example 12

A resin monomer dispersion liquid obtained by dispersing the fine titanium oxide particles obtained in Example 6 in a resin monomer-dissolved liquid of 5% by mass avobenzone (100 parts by mass), pure water (234.99 parts by mass), sodium dodecyl benzene sulfonate (0.01 parts by mass), ethylene glycol dimethacrylate (14.0 parts by mass) and a silicone-based defoamer (1.0 part by mass) was mixed, and stirred using a homogenizer, thereby producing an emulsion.

Next, ultraviolet-shielding composite particles ($TiO_2$/5% avobenzone/PMMA) were produced in the same manner as in Example 6 using the above emulsion.

Figure 12:
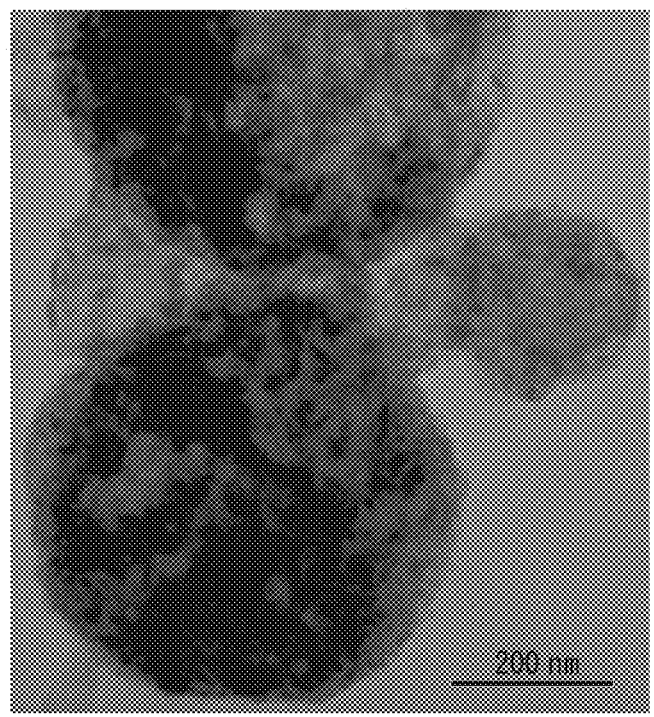
FIG. 12 is a transmission electron microscopic (TEM) image of ultraviolet-shielding composite particles (TiO$_2$/5% avobenzone/PMMA) of Example 12 of the invention.

A transmission electron microscopic (TEM) image of the obtained ultraviolet-shielding composite particles ($TiO_2$/5% avobenzone/PMMA) is illustrated in FIG. 12.

In the ultraviolet-shielding composite particles, not only the resin particles having the fine metal oxide particles encapsulated in the composite particles but also the composite particles having the metal oxide particles exposed on the surfaces of the resin particles, the composite particles having the metal oxide particles partially coated with the resin or particles considered as the metal oxide particles itself, which is not coated with the resin, were observed.

Next, an ultraviolet-shielding composite particle ($TiO_2$/5% avobenzone/PMMA)-containing oil-based dispersion element, which included 30% by mass of the ultraviolet-shielding composite particles ($TiO_2$/5% avobenzone/PMMA), was produced in the same manner as in Example 7 using the above ultraviolet-shielding composite particles ($TiO_2$/5% avobenzone/PMMA).

Next, a simple sunscreen of Example 12, which contained 20% by mass of the ultraviolet-shielding composite particles ($TiO_2$/5% avobenzone/PMMA), was produced in the same manner as in Example 7 using the above ultraviolet-shielding composite particle ($TiO_2$/5% avobenzone/PMMA)-containing oil-based dispersion element.

The spectral transmittance of the obtained simple sunscreen was measured in the same manner as in Example 1. The spectral transmittance of the simple sunscreen is illustrated in FIG. 14.

E. A Simple Sunscreen Using the Ultraviolet-Shielding Composite Particles Having a Changed Particle Diameter.

Example 13

An emulsion was produced in the same manner as in Example 1 except that the components were stirred at 10000 rpm for 15 minutes using a homogenizer AM-7 (manufactured by NISSEI Corporation) instead of at 8000 rpm for 10 minutes.

Next, ultraviolet-shielding composite particles (ZnO/5% avobenzone/PMMA) of Example 13 were produced in the same manner as in Example 1 using the above emulsion.

As a result of measuring the dispersed particle diameter of the ultraviolet-shielding composite particles (ZnO/5% avobenzone/PMMA) in the same manner as in Example 1, the particle diameter at 10 volume % (D10) in the cumulative volume particle size distribution was 194.6 nm, the particle diameter at 50 volume % (D50) was 262.6 nm, and the particle diameter at 90 volume % (D90) was 338.0 nm.

Figure 15:
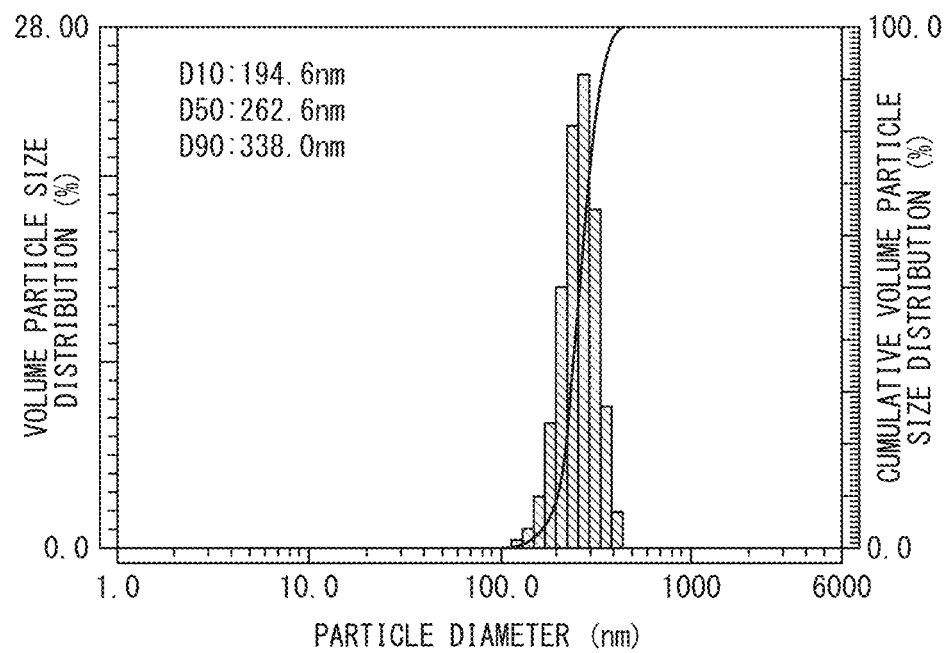
FIG. 15 is a view illustrating the volume particle size distribution and cumulative volume particle size distribution of ultraviolet-shielding composite particles (ZnO/5% avobenzone/PMMA) of Example 13 of the invention.

The volume particle size distribution and cumulative volume particle size distribution of the ultraviolet-shielding composite particle-containing dispersion liquid are illustrated in FIG. 15.

An ultraviolet-shielding composite particle (ZnO/5% avobenzone/PMMA)-containing oil-based dispersion element including 30% by mass of the ultraviolet-shielding composite particles (ZnO/5% avobenzone/PMMA) having a particle diameter at 50 volume % (D50) of 262.6 nm was produced in the same manner as in Example 7 using the above ultraviolet-shielding composite particles (ZnO/5% avobenzone/PMMA).

Next, a simple sunscreen of Example 13, which included 20% by mass of the ultraviolet-shielding composite particles (ZnO/5% avobenzone/PMMA) having a particle diameter at 50 volume % (D50) of 262.6 nm was produced in the same manner as in Example 7 using the above ultraviolet-shielding composite particle (ZnO/5% avobenzone/PMMA)-containing oil-based dispersion element.

The spectral transmittance of the obtained simple sunscreen was measured in the same manner as in Example 1. The spectral transmittance of the simple sunscreen is illustrated in FIG. 18.

Example 14

An emulsion was produced in the same manner as in Example 1 except that the components were stirred at 5000 rpm for 10 minutes using a homogenizer AM-7 (manufactured by NISSEI Corporation) instead of at 8000 rpm for 10 minutes.

Next, ultraviolet-shielding composite particles (ZnO/5% avobenzone/PMMA) of Example 14 were produced in the same manner as in Example 1 using the emulsion obtained above.

As a result of measuring the dispersed particle diameter of the ultraviolet-shielding composite particles (ZnO/5% avobenzone/PMMA) in the same manner as in Example 1, the particle diameter at 10 volume % (D10) was 696.9 nm, the particle diameter at 50 volume % (D50) was 976.9 nm, and the particle diameter at 90 volume % (D90) was 132.8 nm in the cumulative volume particle size distribution.

Figure 16:
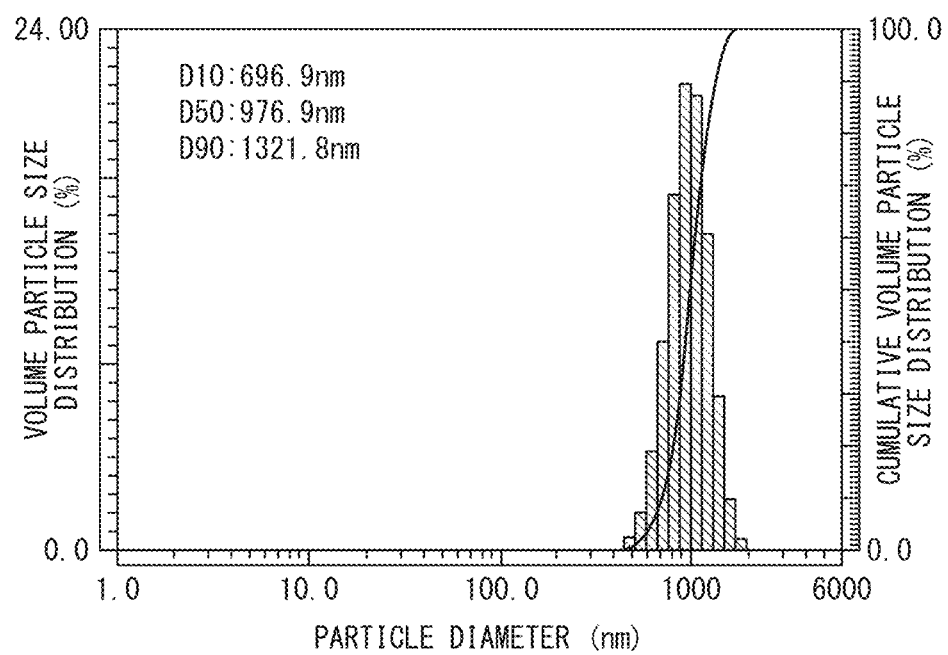
FIG. 16 is a view illustrating the volume particle size distribution and cumulative volume particle size distribution of ultraviolet-shielding composite particles (ZnO/5% avobenzone/PMMA) of Example 14 of the invention.

The volume particle size distribution and cumulative volume particle size distribution of the ultraviolet-shielding composite particle-containing dispersion liquid are illustrated in FIG. 16.

An ultraviolet-shielding composite particle (ZnO/5% avobenzone/PMMA)-containing oil-based dispersion element including 30% by mass of the ultraviolet-shielding composite particles (ZnO/5% avobenzone/PMMA) having a particle diameter at 50 volume % (D50) of 976.9 nm was produced in the same manner as in Example 7 using the above ultraviolet-shielding composite particles (ZnO/5% avobenzone/PMMA).

Next, a simple sunscreen of Example 14, which included 20% by mass of the ultraviolet-shielding composite particles (ZnO/5% avobenzone/PMMA) having a particle diameter at 50 volume % (D50) of 976.9 nm was produced in the same manner as in Example 7 using the above ultraviolet-shielding composite particle (ZnO/5% avobenzone/PMMA)-containing oil-based dispersion element.

The spectral transmittance of the obtained simple sunscreen was measured in the same manner as in Example 1. The spectral transmittance of the simple sunscreen is illustrated in FIG. 18.

Example 15

An emulsion was produced in the same manner as in Example 1 except that the components were stirred at 3000 rpm for 5 minutes using a homogenizer AM-7 (manufactured by NISSEI Corporation) instead of at 8000 rpm for 10 minutes.

Next, ultraviolet-shielding composite particles (ZnO/5% avobenzone/PMMA) of Example 15 were produced in the same manner as in Example 1 using the above emulsion.

As a result of measuring the dispersed particle diameter of the ultraviolet-shielding composite particles (ZnO/5% avobenzone/PMMA) in the same manner as in Example 1, the particle diameter at 10 volume % (D10) was 1396.0 nm, the particle diameter at 50 volume % (D50) was 1914.0 nm, and the particle diameter at 90 volume % (D90) was 2526.5 nm in the cumulative volume particle size distribution.

Figure 17:
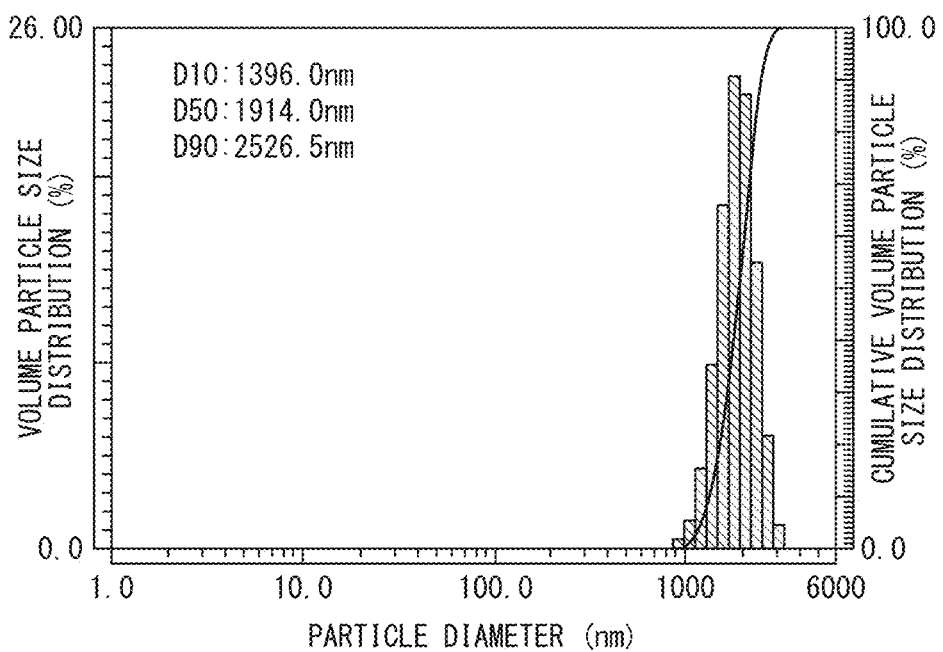
FIG. 17 is a view illustrating the volume particle size distribution and cumulative volume particle size distribution of ultraviolet-shielding composite particles (ZnO/5% avobenzone/PMMA) of Example 15 of the invention.

The volume particle size distribution and cumulative volume particle size distribution of the ultraviolet-shielding composite particle-containing dispersion liquid are illustrated in FIG. 17.

An ultraviolet-shielding composite particle (ZnO/5% avobenzone/PMMA)-containing oil-based dispersion element including 30% by mass of the ultraviolet-shielding composite particles (ZnO/5% avobenzone/PMMA) having a particle diameter at 50 volume % (D50) of 1914.0 nm was produced in the same manner as in Example 7 using the above ultraviolet-shielding composite particles (ZnO/5% avobenzone/PMMA).

Next, a simple sunscreen of Example 15, which contained 20% by mass of the ultraviolet-shielding composite particles (ZnO/5% avobenzone/PMMA) of Example 15 having a particle diameter at 50 volume % (D50) of 1914.0 nm was produced in the same manner as in Example 7 using the above ultraviolet-shielding composite particle (ZnO/5% avobenzone/PMMA)-containing oil-based dispersion element.

The spectral transmittance of the obtained simple sunscreen was measured in the same manner as in Example 1. The spectral transmittance of the simple sunscreen is illustrated in FIG. 18.

INDUSTRIAL APPLICABILITY

When the ultraviolet-shielding composite particles of the invention includes a resin containing an organic ultraviolet absorbent and metal oxide particles having an ultraviolet-shielding function, and have an average particle diameter of 0.05 μm or more and 5 μm or less, since it is possible to prevent the alteration and discoloration of a cosmetic material and the impairment in a feeling of using the product, the burden for contacted skin can be reduced, and the particles can be safely used, it is possible to blend the particles not only into a water-in-oil (W/O) cosmetic material but also into an aqueous cosmetic material, such as an oil-in-water (O/W) cosmetic material, skin toner or sun-screening gel, the formulation of which was difficult in the related art, it is possible to increase the degree of freedom for the formulation of the cosmetic material, and the industrial value is large.

We claim:

1. Ultraviolet-shielding composite particles, comprising: a resin which contains an organic ultraviolet absorbent and metal oxide particles having an ultraviolet-shielding function, the ultraviolet-shielding composite particles having an average particle diameter of 0.05 μm or more and 5 μm or less,
   wherein the metal oxide particles are particles which include one or two or more selected from the group consisting of zinc oxide, titanium oxide, cerium oxide and iron oxide and have an average particle diameter of 0.003 μm or more and 0.1 μm or less,
   a content of the organic ultraviolet absorbent in the ultraviolet-shielding composite particles is 0.1% by mass or more and 80% by mass or less, a content of the metal oxide particles is 1% by mass or more and 80% by mass or less, and
   the metal oxide particles are dispersed in the ultraviolet-shielding composite particles substantially without being exposed on surfaces of the ultraviolet-shielding composite particles.

2. The ultraviolet-shielding composite particles according to claim 1, wherein the resin is a (meth)acrylic resin.

3. The ultraviolet-shielding composite particles according to claim 1 wherein the organic ultraviolet absorbent is one or two or more selected from the group consisting of dibenzoyl methane-based compounds, benzophenone derivatives, para-aminobenzoic acid derivatives, methoxycinnamic acid derivatives and salicylic acid derivatives.

4. A method for manufacturing ultraviolet-shielding composite particles according to claim 1, comprising:

dispersing metal oxide particles having an average particle diameter of 0.003 µm or more and 0.1 µm or less and an ultraviolet-shielding function in 1% by mass or more and 50% by mass or less of dispersant-containing resin monomers with respect to the metal oxide particles to produce a resin monomer dispersion liquid containing the metal oxide particles;

dissolving 0.1% by mass or more and 80% by mass or less of an organic ultraviolet absorbent in the resin monomer dispersion liquid to produce a resin monomer-dissolved liquid containing the metal oxide particles and the organic ultraviolet-shielding absorbent;

suspending or emulsifying the resin monomer-dissolved liquid in pure water including a suspension protectant, a silicone-based defoamer and a crosslinking agent to produce a suspended liquid or an emulsified liquid; and adding a polymerization initiator to the suspended liquid or the emulsified liquid to perform suspension polymerization or emulsion polymerization and generate ultraviolet-shielding composite particles.

5. A method for manufacturing ultraviolet-shielding composite particles according to claim 1, comprising:

dissolving 0.1% by mass or more and 80% by mass or less of an organic ultraviolet absorbent to produce a resin monomer-dissolved liquid containing the organic ultraviolet absorbent;

dispersing 1% by mass or more and 80% by mass or less of metal oxide particles having an average particle diameter of 0.003 µm or more and 0.1 µm or less and an ultraviolet-shielding function in the resin monomer-dissolved liquid to produce a resin monomer dispersion liquid containing the metal oxide particles and the organic ultraviolet absorbent;

suspending or emulsifying the resin monomer dispersion liquid in pure water including a suspension protectant, a silicone-based defoamer and a crosslinking agent to produce a suspended liquid or an emulsified liquid; and adding a polymerization initiator to the suspended liquid or the emulsified liquid to perform suspension polymerization or emulsion polymerization and generate ultraviolet-shielding composite particles.

6. An ultraviolet-shielding composite particle-containing dispersion liquid, in which the ultraviolet-shielding composite particles of claim 1 are dispersed in a dispersion medium, wherein a content of the ultraviolet-shielding composite particles is 1% by mass or more and 80% by mass or less.

7. An ultraviolet-shielding composite particle-containing aqueous dispersion element, in which the ultraviolet-shielding composite particles of claim 1 are dispersed in a dispersion medium including alcohols and water, wherein a content of the ultraviolet-shielding composite particles is 1% by mass or more and 80% by mass or less, a content of the alcohols is 5% by mass or more and 20% by mass or less and a content of water is 15% by mass to 94% by mass.

8. An ultraviolet-shielding composite particle-containing oil-based dispersion element, in which the ultraviolet-shielding composite particles of claim 1 are dispersed in an oily component including a surfactant, wherein a content of the ultraviolet-shielding composite particles is 1% by mass or more and 80% by mass or less, a content of the oily component is 10% by mass or more and 90% by mass or less, and a content of the surfactant is 1% by mass or more and 40% by mass or less.

9. A cosmetic material, comprising:
1% by mass or more and 60% by mass or less of the ultraviolet-shielding composite particles of claim 1.

10. A cosmetic material, comprising:
1% by mass or more and 60% by mass or less of the ultraviolet-shielding composite particle-containing dispersion liquid of claim 6 in terms of the ultraviolet-shielding composite particles.

11. A cosmetic material, comprising:
1% by mass or more and 60% by mass or less of the ultraviolet-shielding composite particle-containing aqueous dispersion element of claim 7 in terms of the ultraviolet-shielding composite particles.

12. A cosmetic material, comprising:
1% by mass or more and 60% by mass or less of the ultraviolet-shielding composite particle-containing oil-based dispersion element of claim 8 in terms of the ultraviolet-shielding composite particles.

13. The ultraviolet-shielding composite particles according to claim 1, wherein 90% by mass or more of the ultraviolet-shielding composite particles have the metal oxide particles that are embedded in the ultraviolet-shielding composite particles to be in an encapsulated state.

14. The ultraviolet-shielding composite particles according to claim 1, wherein 99% by mass or more of the ultraviolet-shielding composite particles have the metal oxide particles that are embedded in the ultraviolet-shielding composite particles to be in an encapsulated state.

* * * * *